United States Patent

Heinen et al.

[11] Patent Number: 5,910,310
[45] Date of Patent: Jun. 8, 1999

[54] PORCINE PARAINFLUENZA VIRUS TYPE 2

[75] Inventors: Ernst Heinen, Echternacherbrück; Norbert Schmeer, Haan; Werner Herbst, Biebertal, all of Germany

[73] Assignee: Bayer Aktiengesellschaft, Leverkusen, Germany

[21] Appl. No.: 08/700,548

[22] PCT Filed: Feb. 22, 1995

[86] PCT No.: PCT/EP95/00642

§ 371 Date: Aug. 30, 1996

§ 102(e) Date: Aug. 30, 1996

[87] PCT Pub. No.: WO95/24214

PCT Pub. Date: Sep. 14, 1995

[30] Foreign Application Priority Data

Mar. 7, 1994 [DE] Germany .............................. 44 07 489

[51] Int. Cl.⁶ ...................... A61K 39/155; A61K 39/295; C12N 7/00
[52] U.S. Cl. .................................. 424/211.1; 435/235.1; 435/236; 424/201.1
[58] Field of Search ............................. 424/209.1, 210.1, 424/211.1, 184.1, 130.1, 199.1; 435/5, 41, 69.1, 69.3, 235.1, 236, 237, 239, 240.2

[56] References Cited

FOREIGN PATENT DOCUMENTS

| 0 013 188 A2 | 1/1979 | European Pat. Off. . |
| 0013188 | 9/1980 | European Pat. Off. . |
| 8808718 | 11/1988 | WIPO . |
| WO 88/08718 | 11/1988 | WIPO . |
| 9002566 | 3/1990 | WIPO . |
| WO 90/02566 | 3/1990 | WIPO . |
| 9307898 | 4/1993 | WIPO . |
| WO 93/07898 | 4/1993 | WIPO . |

OTHER PUBLICATIONS

Chanock et al Parainfluenza virus in Virology Ed Fields Raven Press New York p. 1250, 1985.
Itoh et al. Single amino substitution of sendai virus at the cleavage site of the fusion confers trypsin resistance. J. Gen. Virology 68:2939–2944, 1987.
Christianson, W.T. et al. Swine Health and Production, vol. 2, No. 2, p. 10–28, Apr. 1994.
Crandell, R.A. et al. Journal of Clinical Microbiology, vol. 7, No. 2, pp. 214–218, Feb. 1978.
Fenner, F.J. et al. Veterinary Virology, second edition, pp. 476–478. Academic Press, Inc., San Diego CA, 1993.
Goyal, S.M. et al. The Veterinary Record, vol. 119, No. 14, p. 363, Oct. 1986.
Guenov, I. et al. Zentralblatt fur Veterinarymedizin, vol. 19B (Heft 6), pp. 437–444, abstract only, 1972.
Hernandez Jauregui, P. et al. Veterinaria Mexico, vol. 23, pp. 217–222, abstract only, 1992.
The Veterinary Record, vol. 129, No. 1, p. 19, London Jul. 6, 1991.

*Primary Examiner*—Mary E. Mosher
*Attorney, Agent, or Firm*—Joseph C. Gil

[57] ABSTRACT

The present invention relates to a viral agent as a vaccine component for the protection of pigs against diseases of the respiratory and reproductive tract, based on parainfluenza viruses.

6 Claims, No Drawings

PORCINE PARAINFLUENZA VIRUS TYPE 2

The present invention relates to a viral agent, processes for the culture and replication of this agent and the utilization of this agent on its own or in combination with other bacterial or viral pathogens as a vaccine component for the protection of pigs from diseases of the respiratory and reproductive tract.

At the end of the eighties to the start of the nineties a new pig disease which spread like the plague and was accompanied by high economic losses occurred in North America and Europe. In the meantime, this has been officially called "Porcine Reproductive and Respiratory Syndrome" (PRRS).

The main clinical symptoms of these contagious diseases are fertility disorders in sows and respiratory tract diseases in piglets and fattening pigs.

Besides the irregularly occurring non-specific symptoms such as loss of appetite, apathy and fever, the disease is characterized in sows by late abortions, stillbirths and by the birth of mummified and weak piglets. As a result of the epidemic, symptoms of the mastitis-metritis-agalactia (MMA) complex and return to oestrus occur in large numbers.

In an endemic region are unweaned and weaner piglets in an endemic region are mainly affected at the start of the epidemic, in the further course fattening pigs increasingly fall ill. In this case, besides the mainly occurring diseases of the respiratory tract, other classical pig diseases can also be observed in association at an increased frequency. The epidemic causes considerable economic losses, which results besides the direct animal losses from the decrease in the characteristic production numbers (farrowing and weaning results, pregnancy rate, weight increase).

The primary infectious agent is assumed to be a new RNA virus replicating in pulmonary alveolar macrophages. On the other hand, epidemiological investigations indicate that respiratory and reproductive diseases can be additionally caused or intensified by secondary or multiple infections with other viruses or viruses and bacteria. It is therefore desirable to protect pigs not only against the main causative agent of PRRS, but also against the causative agents which are additionally responsible for respiratory and reproductive diseases.

The present invention relates to:

1. A vaccine against diseases of the respiratory and reproductive tract of pigs, in particular in connection with the disease complex called PRRS, characterized by containing as antigenic material, in whole form or in parts or submits parainfluenza viruses and their variants and mutants in modified live or inactivated form, prepared by conventional or recombinant techniques.
2. Antigens based on parainfluenza viruses which cause diseases of the respiratory and reproductive tract of pigs.
3. A process for the preparation of antigens based on parainfluenza viruses which cause diseases of the respiratory and reproductive tract of pigs, characterized in that parainfluenza viruses are replicated and the antigenic material is isolated in a manner known per se from the virus suspensions thus obtained
4. The use of antigens based on parainfluenza viruses which cause diseases of the respiratory and reproductive tract of pigs for the diagnosis and/or prevention of these diseases.
5. The use of antigens based on parainfluenza viruses which cause diseases of the respiratory and reproductive tract of pigs for the production of diagnostics for the detection of these diseases and for the production of vaccines for the prevention of these diseases.

Antigenic material which may be mentioned is:

1. Complete, live virus particles, obtained by replication of the virus in cell cultures or embryonated chicken eggs.
2. Complete, live, attenuated virus particles, obtained by continuous passages of the virus in primary cell cultures, permanent cell lines, embryonated poultry eggs or experimental animals with subsequent replication in cell cultures or embryonated chicken eggs.
3. Complete, killed virus particles which are prepared by means of conventional processes, such as chemical or physical inactivation.
4. Subunits of the virus particles prepared from virus which is replicated in cell cultures or embryonated eggs.
5. Subunits of the virus particles which are expressed by cell systems by the means of recombinant techniques and can optionally be separated from these or isolated from these.
6. Virus antigens which are expressed in vector systems, by inserting the genome of the virus or parts thereof employed by means of recombinant techniques in genome vectors such as vaccini viruses, herpes viruses, adenoviruses or other suitable vector systems.

Parainfluenza viruses type 2 (PIV-2) are preferably used. PIV-2 which have been isolated from the respiratory or reproductive tract of pigs which exhibit a PRRS-like symptomatology are particularly preferred. The PIV-2 strain having the notation SER, which was deposited according to the Budapest convention on 12.6.1993 in the Collection Nationale des Cultures et de Microorganismes (Institut Pasteur, Paris, France) under the number I-1331, is particularly suitable.

In the vaccines according to the invention, the antigenic material of the parainfluenza viruses can be present in a mixture with antigenic material of other viruses or bacteria. Those which may be mentioned are: Chlamydia, in particular *Chlamydia psittaci* and *Chlamydia pecorum* in concentrations of $10^5$–$10^{10}$ FU[1]/dose, *Erysipelothrix rhusiopathiae* in concentrations of $10^7$–$10^{12}$ CFU/dose, PRRS viruses in concentrations of $10^4$–$10^9$ TCID$^2_{50}$/dose and porcines parvovirus in concentrations of $10^4$–$10^9$ TCID$_{50}$/dose.

A mixture of PIV-2 and Chlamydia, in particular *Chlamydia psittaci* or *Ch. pecorum*, is particularly preferred.

[1]IFU=Inclusion Forming Units
[2]TCID=Tissue Culture Infective Dose

The following terms are used in the following details:

| | |
|---|---|
| Cotransfection | Simultaneous introduction of two different DNA sequences into cells in which viruses can be replicated, with the aim of inducing virus recombinants which contain foreign DNA sequences. The different DNA sequences are (1) foreign DNA which can be inserted in shuttle vectors and (2) the purified genome of the vector virus. |
| Genome vector | Live causative agents, in particular viruses, which are suitable for the insertion of foreign DNA and infect cells or organisms with the foreign DNA inserted in their genome and express the foreign DNA therein. |

| | |
|---|---|
| Immunogens | Peptides or proteins which elicit an immunological reaction in a higher organism and can be expressed in vectors by means of foreign DNA sequences. |
| Cloning | Insertion of foreign DNA sequences in vectors. |
| Plasmid | Extrachromosomal, cyclic DNA sequences which are replicated in procaryotic or eucaryotic cells. |
| Shuttle vector | Bacteriophages or plasmids, in particular bacterial plasmids, which contain inserted foreign DNA which is flanked by DNA sequences of the vector virus. |
| Transfection | Transfer of DNA sequences to procaryotic or eucaryotic cells with the aim of inducing recombinants of the cell genome with the DNA sequences introduced. |
| Vectors | Plasmids, bacteriophages or viruses which carry foreign DNA sequences in their genetic information. |

The replication of the viruses for the production of complete live virus particles is carried out in a manner known per se, on the one hand in tissue cultures of animal cells as primary cells or permanent cell lines, e.g. in porcine cells, monkey cells or bovine cells, preferably in porcine kidney cells such as e.g. the cloned, permanent porcine kidney cell PK15 (ATCC CCL33 or its derivatives) or the primary porcine kidney cell EPK or monkey kidney cells such as the permanent monkey kidney cells BGM (Flow 03-240 or its derivatives) or Vero (ATCC CCL81 or its derivatives) or bovine kidney cells such as the permanent bovine kidney cell MDBK (ATCC CCL22 or its derivatives) and on the other hand in embryonated chicken eggs (e.g. Valo hatching eggs, Lohmann).

Replication in cell cultures is carried out in a manner known per se in stationary roller or carrier cultures in the form of monolayers or in suspension cultures. The growing media employed for the cells are all cell culture media known per se e.g. described in the product catalogue of Gibco BRL GmbH, Dieselstraβe 5, 76344 Eggenstein, such as, in particular, Minimal Essential Medium (MEM), which as essential constituents contains amino acids, vitamins, salts and carbohydrates, completed with buffer substances such as e.g. sodium bicarbonate ($NaHCO_3$) or hydroxyethylpiperazine-N-2-ethanesulphonic acid (Hepes) and optionally animal sera, such as e.g. sera from cattle, horses or their foetuses. Eagles MEM having a content of $NaHCO_3$ of 0.1–5 g/l, preferably 0.5–3 g/l, and foetal calf serum in a concentration of 1–30% by volume, preferably 2–10% by volume, is particularly preferably employed.

The cells and cell lawns used for the replication of the viruses are grown in conventional manner almost to confluence or to the optimal cell density. Before their infection with viruses, the cell growth medium is preferably removed and the cells are preferably washed with virus replication medium. The virus replication medium employed are all cell culture media known per se, such as, in particular, the abovementioned MEM. Infection is then carried out using a virus suspension. In the virus suspension, the virus is diluted in the virus replication medium to a MOI (=multiplicity of infection, corresponds to the ratio of the number of infectious virus particles to the number of cells present) of 0.01–50, preferably 0.1–10.

The replication of the viruses is carried out with or without addition of animal sera. In the case where serum is employed, it is added to the replication medium in a concentration of 1–30% by volume, preferably 2–10% by volume.

Infection and virus replication are carried out at temperatures between room temperature and 40° C., preferably between 32 and 39° C., particularly preferably at 37° C. for several days, preferably up to complete destruction of the infected cells.

The virus-containing medium of the infected cells is worked up further, e.g. by removing the cells and cell debris by means of filtration using pore sizes of e.g. 0.1–0.45 μm and/or centrifugation up to 10,000×g.

Replication in embryonated chicken eggs is carried out in a manner known per se in the allantoic cavity of chicken hatching eggs which have been preincubated for 9–12 days, preferably 10 days, at a temperature of 37–39° C., preferably 38.5° C., and a relative humidity of 30–90%, preferably 50–60%, in a commercially available incubator, preferably a power-driven incubator.

Before inoculation, the hatching eggs used for replication of the viruses are placed standing vertically in the incubator on the pointed end of the egg for 1–3 hours, preferably 2 hours, and then, after preparation of the injection site, infected with 10–200 μl, preferably 75–125 μl, of a virus suspension. In the virus suspension, the virus is diluted in the virus replication medium to a concentration of $10^1$–$10^7$ $TCID_{50}$/ml (50% culture-infectious dose per ml of suspension=the dilution stage at which 50% of the cell cultures employed would be infected), preferably $10^4$–$10^5$ $TCID_{50}$/ml. As the virus replication medium, all cell culture media known per se, such as, in particular, the abovementioned MEM, are employed.

Infection and virus replication are carried out for several days, preferably 2–5 days, particularly preferably 3 days, under the incubation conditions indicated above.

The virus-containing allantoic fluid is obtained by aspiration after opening the calcareous shell and also the periostracum and the chorioallantoic membrane and can be further worked up e.g. by means of filtration using pore sizes of e.g. 0.1–0.45 μm and/or centrifugation up to 10,000×g.

The preparation of attenuated, live virus is carried out in conventional manner by continuous passage and/or alternating passage on the one hand in tissue cultures of animal cells as primary cells or permanent cell lines, e.g. in porcine cells, monkey cells or bovine cells, preferably in porcine kidney cells such as e.g. the cloned, permanent porcine kidney cell PK15 (ATCC CCL33 or its derivatives) or the primary porcine kidney cell EPK or monkey kidney cells such as the permanent monkey kidney cells BGM (Flow 03-240 or its derivatives) or Vero (ATCC CCL81 or its derivatives) or bovine kidney cells such as the permanent bovine kidney cell MDBK (ATCC CCL22 or its derivatives) or canine kidney cells such as the permanent canine kidney cell MDCK (ATCC CCL34 or its derivatives) and on the other hand in embryonate hens', doves' or ducks' eggs, preferably in embryonated chicken eggs (e.g. Valo hatching eggs, Lohmann) or in experimental animals, preferably in small laboratory animals, e.g. in the guinea-pig, rat or mouse, in which the virus replicates without causing serious symptoms of disease.

Passaging in cell cultures is carried out in a manner known per se in stationary cultures in the form of monolayers. The growth media employed for the cells are all cell culture media known per se e.g. described in the product catalogue of Gibco BRL GmbH, Dieselstraβe 5, 76344 Eggenstein, such as, in particular, Minimal Essential Medium (MEM), which as essential constituents contains amino acids, vitamins, salts and carbohydrates, completed with buffer substances such as e.g. sodium bicarbonate ($NaHCO_3$) or hydroxyethylpiperazine-N-2-ethanesulphonic acid (Hepes) and optionally animal sera, such as e.g. sera from cattle, horses or their foetuses. Eagles MEM having a content of $NaHCO_3$ of 0.1–5 g/l, preferably 0.5–3 g/l and foetal calf serum in a concentration of 1–30% by volume, preferably 2–10% by volume, is particularly preferably employed.

The cells and cell lawns used for passaging the viruses are grown in a conventional manner almost up to confluence or to the optimal cell density. Before their infection with viruses, the cell growth medium is preferably removed and the cells are preferably washed with virus replication medium. The virus replication medium employed are all cell culture media known per se, such as, in particular, the abovementioned MEM. Infection with a virus suspension is then carried out. In the virus suspension, the virus is diluted in the virus replication medium to MOI (=multiplicity of infection, corresponds to the ratio of the number of infectious virus particles to the number of cells present) of 0.01–50, preferably 0.1–10.

The replication of the viruses is carried out with or without addition of animal sera. In the case where serum is employed, it is added to the replication medium in a concentration of 1–30% by volume, preferably 2–10% by volume.

Infection and virus replication are carried out at temperatures between room temperature and 40° C., preferably between 30 and 39° C., for several days, preferably up to complete destruction of the infected cells.

The virus-containing medium of the infected cells is used for infection of a fresh cell culture (subsequent passage).

Passaging in embryonated poultry eggs is carried out in a manner known per se in the allantoic cavity of e.g. hens' hatching eggs which have been preincubated for 9–12 days, preferably 10 days, at a temperature of 37–39° C., preferably 38.5° C., and a relative humidity of 30–90%, preferably 50–60%, in a commercially available incubator, preferably a power-driven incubator.

The hatching eggs used for passaging of the viruses are placed in the incubator standing vertically on the pointed end of the egg for 1–3 hours, preferably 2 hours, before inoculation and then infected with 10–200 $\mu$l, preferably 75–125 $\mu$l, of a virus suspension after preparation of the injection site. In the virus suspension, the virus is present in the virus replication medium diluted to a concentration of $10^1$–$10^7$ $TCID_{50}$/ml (50% culture-infectious dose per ml of suspension=the dilution stage at which 50% of the cell cultures employed would be infected), preferably $10^4$–$10^5$ $TCID_{50}$/ml. The replication medium employed are all cell culture media known per se, such as, in particular, the abovementioned MEM.

Infection and virus replication are carried out for several days, preferably 2–5 days, particularly preferably 3 days, under the incubation conditions indicated above.

The virus-containing allantoic fluid is obtained by aspiration after opening the calcareous shell and also the periostracum and the chorioallantoic membrane. It is used for the infection of fresh preincubated, embryonate eggs (subsequent passage).

Passaging in experimental animals is carried out in a manner known per se by parenteral administration of a virus suspension and reisolation of the virus from organs and tissues of the experimental animals.

For passaging in experimental animals, juvenile, small laboratory animals are preferably employed which originate from SPF (specified pathogen-free) breeding, e.g. guinea-pigs (Hsd/Win:DH, Harlan-Winkelmann GmbH, Borchen), rats (Hsd/Win:WU, Harlan-Winkelmann GmbH, Borchen) or mouse (Hsd/Win:NMRI, Harlan-Winkelmann GmbH, Borchen; Balb/C/JICO, Iffa Credo Belgium). The experimental animals are parenterally infected with 0.1–2.0 ml of a virus suspension, e.g. by intradermal, intramuscular, intranasal, intraperitoneal, intravenous or subcutaneous administration. In the virus suspension, the virus is diluted in the virus replication medium such that the experimental animals in each case receive a virus dose of $10^1$–$10^7$ $TCID_{50}$, preferably $10^3$–$10^5$ $TCID_{50}$ (50% culture-infectious dose per ml of suspension=the dilution stage at which 50% of the cell cultures employed would still be infected). The virus replication medium employed are all cell culture media known per se, such as, in particular, the abovementioned MEM.

Virus replication takes place over the course of several days preferably 1–12 days.

The virus is reisolated from tissues, preferably internal organs of the experimental animals, in a manner known per ser. For this purpose, internal organs, e.g. lungs, liver or spleen are removed from the experimental animals. Fine suspensions are prepared in virus replication medium from the organs or parts of the organs by mechanical disruption, e.g. with the aid of scissors and mortars, which are further worked up, e.g. by removing the cells and cell debris by means of filtration using pore sizes of e.g. 0.1–0.45 $\mu$m and/or centrifugation up to 10,000×g. The virus replication medium employed are all cell culture media known per se, such as, in particular, the abovementioned MEM.

The virus-containing medium obtained is used for the infection of new experimental animals (subsequent passages).

The process of subsequent passage is repeated several times, preferably 10–20 times, in the same replication system (homologous passages) or in different replication systems (heterologous passages).

Monitoring of the virus for attenuation is carried out by experimental infection of fully susceptible experimental animals, preferably pigs, with a virus suspension which originates from the last passage of a series of subsequent passages.

If typical disease symptoms still occur, e.g. abortions and stillbirths in pregnant sows or respiratory diseases, further homologous or heterologous continuous passages are carried out starting from the viruses of the last subsequent passages.

If typical disease symptoms no longer occur, the viruses of the last subsequent passage are replicated as described above and the filtrates or centrifugation supernatants of virus-containing culture supernatants or allantoic fluid are used for the production of vaccines.

Replication of the viruses for the preparation of killed virus particles is carried out in a conventional manner on the one hand in tissue cultures of animal cells as primary cells or permanent cell lines, e.g. in porcine cells, monkey cells or bovine cells, preferably in porcine kidney cells such as e.g. the cloned, permanent porcine kidney cell PK15 (ATCC CCL33 or its derivatives) or the primary porcine kidney cell EPK or monkey kidney cells such as the permanent monkey kidney cells BGM (flow 03-240 or its derivatives) or Vero (ATCC CCL81 or its derivatives) or bovine kidney cells such as the permanent bovine kidney cell MDBK (ATCC CCL22 or its derivatives) and on the other hand in embryonate hens' eggs (e.g. Valo hatching eggs, Lohmann).

Replication in cell cultures is carried out in a manner known per se in stationary roller or carrier cultures in the form of monolayers or in suspension cultures. The growing media employed for the cells are all cell culture media known per se e.g. described in the product catalogue of Gibco BRL GmbH, Dieselstraβe 5, 76344 Eggenstein, such as, in particular, Minimal Essential Medium (MEM), which as essential constituents contains amino acids, vitamins, salts and carbohydrates, completed with buffer substances such as e.g. sodium bicarbonate ($NaHCO_3$) or hydroxyethylpiperazine-N-2-ethanesulphonic acid (Hepes) and optionally animal sera, such as e.g. sera of cattle, horses or their foetuses. Eagles MEM having a content of $NaHCO_3$ of 0.1–5 g/l, preferably 0.5–3 g/l and also foetal calf serum in a concentration of 1–30% by volume, preferably 2–10% by volume, is particularly preferably employed.

The cells and cell lawns used for replication of the viruses are grown in conventional manner almost to confluence or to the optimal cell density. Before their infection with viruses, the cell growth medium is preferably removed and the cells preferably are washed with virus replication medium. The virus replication medium employed are all cell culture media known per se, such as, in particular, the abovementioned MEM. Infection is then carried out with a virus suspension. In the virus suspension, the virus is diluted in the virus replication medium diluted to a MOI (=multiplicity of infection, corresponds to the ratio of the number of infectious virus particles to the number of cells present) of 0.01–50, preferably 0.1–10.

The replication of the viruses is carried out with or without addition of animal sera. In the case where serum is employed, it is added to the replication medium in a concentration of 1–30% by volume, preferably 2–10% by volume.

Infection and virus replication are carried out at temperatures between room temperature and 40° C., preferably between 32 and 39° C., particularly preferably at 37° C. for several days, preferably up to complete destruction of the infected cells.

The virus-containing medium of the infected cells is worked up further, e.g. by removing the cells and cell debris by means of filtration using pore sizes of e.g. 0.1–0.45 μm and/or centrifugation up to 10,000×g.

Replication in embryonated chicken eggs is carried out in a manner known per se in the allantoic cavity of chicken hatching eggs which have been preincubated for 9–12 days, preferably 10 days, at a temperature of 37–39° C., preferably 38.5° C., and a relative humidity of 30–90% preferably 50–60%, in a commercially available incubator, preferably a power-driven incubator.

The hatching eggs used for replication of the viruses are placed in the incubator standing vertically on the pointed end of the egg for 1–3 hours, preferably 2 hours, before inoculation and then infected with 10–200 μl, preferably 75–125 μl, of a virus suspension after preparation of the injection site. In the virus suspension, the virus is present in the virus replication medium diluted to a concentration of $10^1$–$10^7$ $TCID_{50}$/ml (50% culture-infectious dose per ml of suspension=the dilution stage at which 50% of the cell cultures employed would be infected), preferably $10^4$–$10^5$ $TCID_{50}$/ml. The virus replication medium employed are all cell culture media known per se, such as, in particular, the abovementioned MEM.

Infection and virus replication are carried out for several days, preferably 2–5 days, particularly preferably 3 days, under the incubation conditions indicated above.

The virus-containing allantoic fluid is obtained by aspiration after opening the calcareous shell and also the periostracum and the chorioallantoic membrane and can be further worked up e.g. by means of filtration using pore sizes of e.g. 0.1–0.45 μm and/or centrifugation up to 10,000×g.

Inactivation of the viruses is carried out in a manner known per se by physical processes, e.g. by the action of heat, UV or gamma irradiation or preferably by chemical processes, e.g. by the action of ethanol, formaldehyde, β-propiolactone and preferably by ethyleneamines.

Chemical inactivation is carried out in a manner known per se in suitable reaction vessels which have a device for maintaining a constant reaction temperature and also for continuous agitation of the reaction mixture (e.g. fermenters). Inactivating agents employed are preferably ethyleneamines, particularly preferably 2-bromoethylamine hydrobromide (2-BEA) in a concentration of 1–10 mmol/l, preferably 2.5–7.5 mmol/l.

A virus suspension having a concentration of $10^{4.0}$14 $10^{9.0}$ $TCID_{50}$/ml, preferably $10^{5.0}$–$10^{8.0}$ $TCID_{50}$/ml which originates from one or more virus replications is adjusted to a pH of 8.1–8.7, preferably 8.3–8.5, before addition of the 2-BEA solution.

Inactivation is carried out at 4–40° C., preferably 23–37° C., particularly preferably at 36–37° C., for 6–48 hours, preferably 16–20 hours.

Excess 2-BEA is neutralized by addition of hydrolysing agents after conclusion of the inactivation. For this purpose, in particular, sodium thiosulphate that is added in a final concentration of 40–80 mmol/l, preferably 50 mmol/l, is suitable. Neutralization is carried out at 4–40° C., preferably at 2–8° C., for 2–16 hours, preferably 4–8 hours.

Replication of the viruses for the preparation of sub-units is carried out in the manner known per se on the one hand in tissue cultures of animal cells as primary cells or permanent cell lines, e.g. in porcine cells, monkey cells or bovine cells, preferably in kidney cells such as e.g. the cloned, permanent porcine kidney cell PK15 (ATCC CCL33 or its derivatives) or the primary porcine kidney cell EPK or porcine kidney cells such as the permanent porcine kidney cells BGM (Flow 03-240 or its derivatives) or Vero (ATCC CCL81 or its derivatives) or bovine kidney cells such as the permanent bovine kidney cell MDBK (ATCC CCL22 or its derivatives) and on the other hand in embryonated chicken eggs (e.g. Valo hatching eggs, Lohmann).

Replication in cell cultures is carried out in a manner known per se in stationary roller or carrier cultures in the form of monolayers or in suspension cultures. Growing media employed for the cells are all cell culture media known per se e.g. described in the product catalogue of Gibco BRL GmbH, Dieselstraβe 5, 76344 Eggenstein, such as, in particular, Minimal Essential Medium (MEM), which as essential constituents contains amino acids, vitamins, salts and carbohydrates, completed with buffer substances such as e.g. sodium bicarbonate ($NaHCO_3$) or hydroxyethylpiperazine-N-2-ethanesulphonic acid (Hepes) and optionally animal sera, such as e.g. sera of cattle, horses or their foetuses. Eagles MEM having a content of $NaHCO_3$ of 0.1–5 g/l, preferably 0.5–3 g/l and also foetal calf serum in a concentration of 1–30% by volume, preferably 2–10% by volume, is particularly preferably employed.

The cells and cell lawns used for replication of the viruses are grown in conventional manner almost to confluence or to the optimal cell density. Before its infection with viruses, the cell growth medium is preferably removed and the cells are preferably washed with virus replication medium. The virus replication medium employed are all cell culture media known per se, such as, in particular, the abovementioned MEM. Infection with a virus suspension is then carried out. In the virus suspension, the virus is diluted in the virus replication medium to a MOI (=multiplicity of infection, corresponds to the ratio of the number of infectious virus particles to the number of cells present) of 0.01–50, preferably 0.1–10.

Replication of the viruses is carried out with or without addition of animal sera. In the case where serum is employed, this is added to the replication medium in a concentration of 1–30% by volume, preferably 2–10% by volume.

Infection and virus replication are carried out at temperatures between room temperature and 40° C., preferably between 32 and 39° C., particularly preferably at 37° C., for several days, preferably up to complete destruction of the infected cells.

The virus-containing medium of the infected cells is worked up further, e.g. by removal of the cells and cell debris by means of filtration using pore sizes of e.g. 0.1–0.45 μm and/or centrifugation up to 10,000×g.

Replication in embryonated chicken eggs is carried out in a manner known per se in the allantoic cavity of chicken hatching eggs which have been preincubated for 9–12 days, preferably 10 days, at a temperature of 37–39° C., preferably 38.5° C. and a relative humidity of 30–90%, preferably 50–60%, in a commercially available incubator, preferably a power-driven incubator.

The hatching eggs used for replication of the viruses are placed in the incubator standing vertically on the pointed end of the egg for 1–3 hours, preferably 2 hours, before inoculation and then infected with 10–200 μl, preferably 75–125 μl, of a virus suspension after preparation of the injection site. In the virus suspension, the virus is diluted to in the virus replication medium diluted to a concentration of $10^1$–$10^7$ $TCID_{50}$/ml (50% culture infectious dose per ml of suspension=the dilution stage at which 50% of the cell cultures employed would still be infected), preferably $10^4$–$10^5$ $TCID_{50}$/ml. The virus replication medium employed are all cell culture media known per se, such as, in particular, the abovementioned MEM.

Infection and virus replication are carried out for several days, preferably 2–5 days, particularly preferably 3 days, under the incubation conditions indicated above.

The virus-containing allantoic fluid is obtained by aspiration after opening the calcareous shell and also the periostracum and the chorioallantoic membrane and can be further worked up e.g. by means of filtration using pore sizes of e.g. 0.1–0.45 μm and/or centrifugation up to 10,000×g.

Virus isolation is achieved by isopycnic or zonal centrifugation in e.g. sucrose density gradients. For this purpose, the virus-containing medium or the allantoic fluid is subjected after removal of the cell debris to a zonal centrifugation at 100,000×g until the virus particles are pelleted. A purer preparation of the virus particles results by zonal centrifugation in an aqueous solution having a higher density than the virus-containing medium. The aqueous solution used can be e.g. a 30–60% w/w, preferably 35–50% w/w, buffered solution of sucrose. A still higher degree of purity is achieved by centrifugation in density gradients. For this purpose, the virus purified from cells and cell debris and concentrated by means of zonal centrifugation is isolated by an isopycnic or zonal density gradient centrifugation in a density gradient of e.g. 30 to 50% w/w sucrose in buffered aqueous solution at a centrifugal acceleration of e.g. 100,000 to 150,000×g.

The virus concentrates thus obtained are treated with detergents.

Suitable detergents are:

Anionic surfactants, such as sodium laurylsulphate, fatty alcohol ether sulphates, mono-/dialkyl polyglycol ether orthophosphate monoethanolamine salt, calcium alkylaryl-sulphonate, sodium deoxycholate, cationic surfactants, such as cetyltrimethylammonium chloride, ampholytic surfactants, such as di-sodium N-lauryl-iminodipropiont or lecithin, non-ionic surfactants, e.g. polyoxyethylated castor oil, polyoxyethylated sorbitan monooleate, sorbitan monostearate, glycerol monostearate, polyoxyethylene stearate, alkylphenol polyglycol ethers.

Non-ionic detergents may preferably be mentioned: Non-ionic, water-soluble emulsifiers having an HLB (hydrophilic-lipophilic balance) of greater than 10, e.g. emulsifier NP 40® (Bayer AG), alkylaryl polyglycol ether; Renex 678® (Atlas Chemical Industries), polyoxyethylene alkylaryl ether; Tween 20® (Atlas), polyoxyethylene sorbitan monopalmitate; Myri 53® (Atlas), polyoxyethylene stearate; Atlas G 3707®, polyoxyethylene lauryl ether; Atlas G 3920®, polyoxyethylene oleyl ether; Atlas G 9046 T®, polyoxyethylene mannitan monolaurate; emulsifier 1371 B® (Bayer AG), alkyl polyglycol ether; emulsifier 1736® (Bayer AG), alkyl polyglycol ether (oleyl polyglycol ether); emulsifier OX® (Bayer AG), alkyl polyglycol ether (dodecyl polyglycol ether); Ninox BM-2® (Stepan Chemical Co.) ethoxyethylated nonylphenol; Triton X-100® (Rohm an Haas Co.), isooctylphenolpolyethoxy-ethanol; Cremophor EL®, Nonidet P 40® (Shell).

The detergents are used in diluted form aqueous solutions. Solutions may be mentioned having a 0.1 to 10 per cent by volume, preferably having a 0.5 to 5 per cent by volume, particularly preferably about 1 per cent by volume, detergent content.

The detergent solution is added to the virus concentrate in the volume ratio of about 1:1 to about 10:1. Preferably, the ratio of detergent solution to virus concentrate is of about 3:1.

Detergent treatment is carried out continuous agitation of the mixture at temperatures between 0 and about 24° C., preferably between 2 and 8° C. The detergent treatment lasts 15 minutes to 2 days, preferably 6 to 18 hours. To improve the detergent treatment, the mixture can additionally be subjected to ultrasonic treatment.

The particles which are not dissolved during this treatment are removed, preferably by filtration or centrifugation at e.g. 150,000×g. The filtrate or the centrifugation supernatant thus obtained can be stored at low temperatures (0 to −70° C.) until it is processed further.

The glycoproteins of the virus particles contained in the lysate are isolated by treatment with lectins. Lectins are proteins or glycoproteins from plants, especially their seeds, microorganisms, vertebrates and invertebrates, which specifically bind sugars and their conjugates. Lectins are used which recognize and bind glycoproteins from paramyxoviruses. Lectins are preferably used which recognize mannose and/or glucose and their conjugates. Lectins from Canavalia ensiformis, Lens culinaris, Lathygros odoratus, Pisum sativum, Vicia faba, Sambucus nigra, Glycine max, Ulex europaens, Helix promatia, Phytolacca americana, Lycopersicon esculentum, Datura stramonium, Bandeiraea simplificolia may be mentioned especially.

The lectins are used in water-soluble or water-insoluble form. In water-insoluble form they are preferably immobilized by coupling to inert matrixes such as e.g. dextrans, agaroses or celluloses as suspensions or gels. Concanavalin A-agarose, concanavalin A-Sepharose, lentil lectin-Sepharose, agarose-wheatgerm lectin and Helix pomatia lectin-Sepharose may be mentioned especially.

The lectins are employed in form of a detergent- and salt-containing solution, suspension or of a gel. For this, both the lysate and the lectin solution, lectin suspension or the lectin gel employed is previously treated with sufficient sodium chloride and the known lectin-stabilizing salts that a concentration of sodium chloride of 0.5 to 2, preferably 0.7 to 1.2, mol/l achieved. The concentration of the lysates is preferably carried out by dialysis. The concentration of the lectin-salts necessary is known from the prior art and is specific for the lectins to be employed. The lectin solution, the lectin suspension or the lectin gel is moreover treated in the same concentration with the detergent employed for the treatment of the lysates, such that lysate and lectin solution have identical concentrations of salt and detergent.

About 1 to 150 mg, preferably 1 to 50 mg, particularly preferably 5 to 20 mg, of pure lectin are used per ml of solution, suspension or gel. A sufficient amount of the lectin solution, suspension or the lectin gel is added to the lysate that 0.01 to 50 mg, preferably 0.1 to 20 mg, particularly preferably 0.5 to 5 mg, of lectin are employed per mg of total protein. The lectin treatment is carried out at 0 to about 24° C., preferably at 2 to 8° C. for about 10 minutes to 3 days, preferably 1 hour to 2 days.

The reaction of the lectins with the glycoproteins can also be carried out by means of column chromatography, where the lysate is being brought into contact with the lectin immobilized on a gel-like matrix in a chromatography column.

The glycoprotein-lectin complex is separated from the solution or suspension by established methods. It can be achieved by centrifugation, filtration or, in the case of chromatography, by washing.

The concentration of detergent and/or salt of the lectin-glycoprotein containing suspensions or gels obtained in these processes can be adjusted to physiologically tolerable range or eliminated by filtration, centrifugation, dialysis or other washing processes.

The suspensions or gels of the lectin-glycoprotein complexes thus obtained can be used directly as antigenic material. Depending on the content of the glycoprotein bound to lectin, they can be further concentrated or diluted.

The suspensions or gels of the lectin-glycoprotein complexes can be stored at temperatures below 8° C. They can also be freeze-dried.

For the preparation of antigenic material, the glycoproteins can be isolated from the lectin-glycoprotein complex containing suspensions or gels. Therefor, the suspensions or gels are treated with a salt-containing, aqueous sugar solution.

The nature of the sugar to be employed depends on the specificity of the lectins used. The concentration of the sugar is 0.1 to 1 mol/l, preferably 0.1 to 0.5 mol/l, particularly preferably 0.3 to 0.5 mol/l. Concentration and composition of the salt content corresponds to that of the glycoprotein-lectin complex containing suspensions or gels.

The treatment of the sugar solution is carried out at 0 to about 24° C., preferably at 2 to 8° C. The treatment is for about 15 minutes to 4 days, preferably 1 hour to 2 days, particularly preferably 10 to 24 hours.

The glycoproteins eluted in this way are isolated from the lectins by centrifugation, filtration or by other customary separation processes (e.g. chromatography). The concentrations of detergent, salt and sugar in the resulting preparations can be adjusted as already described above.

The isolated glycoproteins thus obtained can be used as antigenic material. The glycoprotein content can be adjusted by concentration or dilution.

The preparations are stored in soluble form at temperatures below 0° C. or in lyophilized form.

For the preparation of subunits of the virus particles by the recombinant route, the virus genome is obtained first.

To obtain the virus genome, replication of the viruses is carried out in a manner known per se on the one hand in tissue cultures of animal cells as primary cells or permanent cell lines, e.g. in porcine cells, simian cells or bovine cells, preferably in porcine kidney cells such as e.g. the cloned, permanent porcine kidney cell PK15 (ATCC CCL33 or its derivatives) or the primary porcine kidney cell EPK or monkey kidney cells such as the permanent monkey kidney cells BGM (Flow 03-240 or their derivatives) or Vero (ATCC CCL81 or their derivatives) or bovine kidney cells such as the permanent bovine kidney cell MDBK (ATCC CCL22 or its derivatives) and on the other hand in embryonated chicken eggs (e.g. Valo hatching eggs, Lohmann).

Replication in cell cultures is carried out in a manner known per se in stationary roller or carrier cultures in the form of monolayers or in suspension cultures. Growing media employed for the cells are all cell culture media known per se e.g. described in the product catalogue of Gibco BRL GmbH, Dieselstraβe 5, 76344 Eggenstein, such as, in particular, Minimal Essential Medium (MEM), which as essential constituents contains amino acids, vitamins, salts and carbohydrates, completed with buffer substances such as e.g. sodium bicarbonate ($NaHCO_3$) or hydroxyethyl-piperazine-N-2-ethanesulphonic acid (Hepes) and optionally animal sera, such as e.g. sera of cattle, horses or their foetuses. Eagles MEM having a content of $NaHCO_3$ of 0.1–5 g/l, preferably 0.5–3 g/l and also foetal calf serum in a concentration of 1–30% by volume, preferably 2–10% by volume, is particularly preferably employed.

The cells and cell lawns used for replication of the viruses are grown in a conventional manner almost to confluence or to the optimal cell density. Before their infection with viruses, the cell growth medium is preferably removed and the cells are preferably washed with virus replication medium. The virus replication medium employed are all cell culture media known per se, such as, in particular, the abovementioned MEM. Infection is then carried out using a virus suspension. In the virus suspension, the virus is diluted in the virus replication medium to a MOI (=multiplicity of infection, corresponds to the ratio of the number of infectious virus particles to the number of cells present) of 0.01–50, preferably 0.1–10.

Replication of the viruses is carried out with or without addition of animal sera. In the case where serum is employed, it is added to the replication medium in a concentration of 1–30% by volume, preferably 2–10% by volume.

Infection and virus replication are carried out at temperatures between room temperature and 40° C., preferably between 32 and 39° C., particularly preferably at 37° C. for several days, preferably up to complete destruction of the infected cells.

The virus-containing medium of the infected cells is further worked up, e.g. by removal of the cells and cell debris by means of filtration using pore sizes of e.g. 0.1–0.45 μm and/or centrifugation at up to 10,000×g.

Replication in embryonated chicken eggs is carried out in a manner known per se in the allantoic cavity of chicken hatching eggs which have been preincubated for 9–12 days, preferably 10 days, at a temperature of 37–39° C., preferably 38.5° C., and a relative humidity of 30–90%, preferably 50–60%, in a commercially available incubator, preferably a power-driven incubator.

The hatching eggs used for replication of the viruses are stored in the incubator standing vertically on the pointed end of the egg for 1–3 hours, preferably 2 hours, before inoculation and then infected with 10–200 μl, preferably 75–125

μl, of a virus suspension after preparation of the injection site. In the virus suspension, the virus is in the virus replication medium diluted to a concentration of $10^1$–$10^7$ $TCID_{50}$/ml (50% culture-infectious dose per ml of suspension=the dilution stage at which 50% of the cell cultures employed would be infected), preferably $10^4$–$10^5$ $TCID_{50}$/ml. The virus replication medium employed are all cell culture media known per se, such as, in particular, the abovementioned MEM.

Infection and virus replication are carried out for several days, preferably 2–5 days, particularly preferably 3 days, under the incubation conditions indicated above.

The virus-containing allantoic fluid is obtained by aspiration after opening the calcareous shell and also the periostracum and the chorioallantoic membrane and can be further worked up e.g. by means of filtration using pore sizes of e.g. 0.1–0.45 μm and/or centrifugation at 10,000×g.

Virus purification or isolation is achieved by isopycnic or zonal centrifugation in e.g. sucrose density gradients. For this purpose, the virus-containing medium or the allantoic fluid is subjected after removal of the cell debris to a zonal centrifugation at 100,000×g until the virus particles are pelleted. A purer preparation of the virus particles results by zonal centrifugation in an aqueous solution having a higher density than the virus-containing medium. The aqueous solution used can be e.g. a 30–60% w/w, preferably 35–50% w/w, buffered solution of sucrose. A still higher degree of purity is achieved by centrifugation in density gradients. For this purpose, the virus purified from cells and cell debris and concentrated by means of zonal centrifugation is isolated by an isopycnic or zonal density gradient centrifugation in a density gradient of e.g. 30 to 50% w/w sucrose in buffered aqueous solution at a centrifugal acceleration of e.g. 100,000 to 150,000×g.

To obtain suitable genes which code for immunogenic proteins, the virus genome is first isolated from the purified virus particles. The native virus RNA is preferably obtained by treatment of the purified virus particles with detergent- and protease-containing aqueous solutions.

Anionic, cationic, amphoteric and non-ionic detergents are employed. Ionic detergents, preferably sodium dodecylsulphate, are preferably employed in a concentration 0.1–10% by volume, preferably 0.5–3% by volume.

Proteases employed are those which act in the presence of detergents, such as e.g. pronase and, preferably, proteinase K. The proteases are employed in a concentration 0.01–10 mg/ml, preferably 0.05–0.5 mg/ml.

Preferably, aqueous, buffered solutions with supplemented RNase inhibitors are used.

Buffer substances used are salts of weak acids with strong bases such as e.g. tris(hydroxymethyl)-aminomethane, and salts of strong acids with weak bases such as e.g. primary phosphates or mixtures thereof. Tris(hydroxymethyl)-aminomethane is preferably used. The buffer substances are employed in concentrations which ensure a pH at which the RNA is not denatured. pHs of 6–8.5 are preferred, particularly preferably of 7–8.

RNase inhibitors used are e.g. ribonucleoside-vanadyl complexes, protein inhibitors (e.g. RNAguard®/Pharmacia) or preferably diethyl pyrocarbonate (DEPC) in concentrations of 0.01–2% by volume, preferably 0.1–0.5% by volume.

The lipophilic substances of the virus lysate are then extracted using solvents such as e.g. phenol, chloroform or mixtures thereof. Extraction is carried out in one or more stages.

The RNA is precipitated out of the remaining aqueous phase by means of aqueous solutions containing alcohols such as e.g. ethanol or isopropanol and monovalent chloride or acetate salts such as e.g. sodium chloride, sodium acetate or potassium acetate.

The concentration of the alcohols is between 40 and 100% by volume, preferably 60 and 80% by volume and that of the chloride or acetate salts is between 0.01 and 1 mol/l, preferably 0.1 to 0.8 mol/l.

The precipitated RNA is recovered from the aqueous solution e.g. by centrifugation and dissolved again in an aqueous solution e.g. DEPC-water. This aqueous solution preferably contains buffer substances such as e.g. tris (hydroxymethyl)-aminomethane in concentrations of 1–100 mmol/l, preferably 10–50 mmol/l, possibly supplemented with ethylenediamine tetraacetate (EDTA) in concentrations of 0.1–10 mmol/l, preferably 1–10 mmol/l or dithiothreitol (DTT) in concentrations of 0.1–10 mmol/l, preferably 1–10 mmol/l.

The isolated RNA is stored at temperatures below −65° C.

Another method for RNA isolation is e.g. RNA extraction using guanidinium thiocyanate and subsequent caesium chloride density gradient centrifugation of the virus lysate.

Methods for RNA isolation are described in: J. Sambrook, E. F. Fritsch and T. Maniatis (Editor), Molecular Cloning, A Laboratory Manual, 2nd edition, Cold Spring Harbor Laboratory Press, 1989.

The identification of suitable genes is carried out using the isolated virus genome e.g. by:

a) RNA/DNA hybridization of the genome using known gene probes. Suitable gene probes used are DNA probes having nucleotide sequences of known genes for immunogens of related virus strains, such as e.g. simian virus 5 or canine parainfluenza virus 2.

b) Preparation of a complementary DNA (cDNA), cloning of the CDNA in e.g. bacterial plasmids such as e.g. pBR322 to concentrate viral DNA and hybridization of the cloned DNA by means of known gene probes. Suitable gene probes used are DNA probes having nucleotide sequences of known genes for immunogens of related virus strains, such as e.g. simian virus 5 or canine parainfluenza virus 2.

c) Preparation of a complementary DNA (cDNA) and cloning of the cDNA in plasmid expression vectors such as e.g. pUC18/19 or puC 118/119 or in λ-bacteriophage expression vectors such as e.g. λgt11 and its derivatives or λZAP or λORF8. The identification of the genes is carried out by detection of their expressed immunogens with the aid of antibodies which are detected directly or indirectly e.g. by means of immunofluorescence or immunoprecipitation. Suitable antibodies are those which react with immunogens of related virus strains, such as e.g. simian virus 5 or canine parainfluenza virus 2.

d) Preparation of a complementary DNA (CDNA) and cloning of the cDNA in e.g. bacterial plasmids to concentrate viral DNA. The viral DNA of the clones is sequenced and investigated for sequence homologies using known genes of related virus strains, such as e.g. simian virus 5 or canine parainfluenza virus 2.

e) Sequencing of the cDNA during its preparation and investigation for sequence homologies with known genes of related virus strains, such as e.g. simian virus 5 or canine parainfluenza virus 2.

f) Combinations of the methods a) to e).

Methods for RNA/DNA and DNA/DNA hybridization, preparation of cDNA, cloning of DNA in plasmid and bacteriophage vectors, sequencing of DNA and methods for the immunological detection of expressed immunogens are described in:

J. Sambrook, E. F. Fritsch and T. Maniatis (Editor), Molecular Cloning, A Laboratory Manual, 2nd edition, Cold Spring Harbor Laboratory Press, 1989

F. M. Ausubel, Current protocols in molecular biology 1987–1988, John Wiley & Sons, New York, 1987

A. Mayr, Virologische Arbeitsmethoden (Virological Working Methods), Volume III, Gustav Fischer Verlag, Stuttgart, 1989

Those genes are selected in which, using the above-mentioned methods, a nucleotide sequence can be detected which codes for one or more immunogens.

As an example, in the sequence listing (below) are given the nucleotide sequence and the corresponding amino acid sequence of the neuraminidase-hemagglutinin and of the fusion-protein-gene of the Parainfluenza virus type 2 geposed at CNCM under the number I-1331.

The expression of the genes for the production of the immunogens is carried out e.g. by:

a) Stable integration of the genes in the form of complementary DNA into cellular DNA of cells. The genes are cloned beforehand into suitable shuttle vectors. A suitable virus for this is, for example, simian virus 40 (SV40) as well as plasmid expression vectors, which are suitable to be selected and replicated in procaryotes (e.g. *E. coli*) and possess regulatory elements for the expression of foreign DNA in higher cells.

Suitable plasmid expression vectors are e.g. plasmid vectors based on SV40, such as pMSG, pSVT7 or pMT2, or plasmid vectors based on Ebbstein-Barr virus such as pHEBo or p205.

The cloned DNA is isolated and purified by means of the methods described above and inserted in eucaryotic cells by transfection.

Suitable cells are animal cells, in particular permanent cell lines, such as e.g. the porcine kidney cell PK15 (ATCC CCL33 or its derivatives), the monkey kidney cell BGM (Flow 03-240 or its derivatives) or Vero (ATCC CCL81 or its derivatives), the bovine kidney cell MDBK (ATCC CCL22 or its derivatives), the canine kidney cell MDCK (ATCC CCL34 or its derivatives) or the rabbit kidney cell RK-13 (ATCC CCL37).

Transfection is carried out e.g. in the form of calcium phosphate-DNA coprecipitates or by the DEAE/dextran method, the liposome method or by electroporation.

Methods for cloning of the selected genes in suitable vectors and for transfection of the cloned genes in higher cells are described in detail in J. Sambrook, E. F. Fritsch and T. Maniatis (Editor), Molecular Cloning, A Laboratory Manual, 2nd edition, Cold Spring Harbor Laboratory Press, 1989 and F. M. Ausubel, Current protocols in molecular biology 1987–1988, John Wiley & Sons, New York, 1987.

Cell culture supernatants or cell lysates of cells treated in such a way are tested for the presence of expressed immunogens with the aid of antibodies which are detected directly or indirectly e.g. by means of immunofluorescence or immunoprecipitation. Suitable antibodies are those which react with immunogens of related virus strains, such as e.g. simian virus 5 or canine parainfluenza virus 2.

b) Cloning of the genes in the form of complementary DNA in suitable expression vectors for procaryotic or eucaryotic cells.

Suitable vectors are e.g. (i) bacterial plasmid expression vectors, (ii) viral expression vectors for bacteria or (iii) viral expression vectors for eucaryotic cells in which the cloned gene is expressed.

re (i)

Suitable bacterial plasmid expression vectors are e.g. pUC18/19 or pUC 118/119. After cloning of the DNA into the plasmid, it is inserted in procaryotic cells, preferably bacteria, and replicated. A suitable bacterium is e.g. *Escherichia coli* K12 and its derivatives.

The plasmid is incorporated in the procaryotic cell by e.g. calcium phosphate-DNA coprecipitation or electroporation.

re (ii)

Suitable viral expression vectors for bacteria are λ-bacteriophage vectors such as e.g. λgt11 and derivatives, λZAP or λORF8. The replication of the λ-bacteriophage vectors is in particular carried out in *Escherichia coli* e.g. *E. coli* K12 and its derivatives.

re (iii)

Suitable viral expression vectors for eucaryotic cells are e.g. simian virus 40, adenoviruses, herpes simplex virus or baculoviruses. The replication of the viral vectors is carried out in appropriate cell systems. Methods for cloning of the selected genes in suitable expression vectors and their use in appropriate expression systems are described in detail in J. Sambrook, E. F. Fritsch and T. Maniatis (Editor), Molecular Cloning, A Laboratory Manual, 2nd edition, Cold Spring Harbor Laboratory Press, 1989 and F. M. Ausubel, Current protocols in molecular biology 1987–1988, John Wiley & Sons, New York, 1987.

The expressed immunogens are used as antigens either directly in the form of the expression systems (culture substrate and/or cells) or after preparation and purification by means of biochemical and/or immunological methods and optionally after concentration or dilution.

Suitable processes for purification are e.g. affinity or gel chromatography processes in which the immunogens are separated or isolated from the expression system, optionally after detergent treatment.

To prepare virus antigens expressed by vector systems the virus genome is obtained first.

To obtain the virus genome, replication of the viruses is carried out in a manner known per se on the one hand in tissue cultures of animal cells as primary cells or permanent cell lines, e.g. in porcine cells, simian cells or bovine cells, preferably in porcine kidney cells such as e.g. the cloned, permanent porcine kidney cell PK15 PK15 (ATCC CCL33 or its derivatives) or the primary porcine kidney cell EPK or monkey kidney cells such as the permanent monkey kidney cells BGM (Flow 03-240 or its derivatives) or Vero (ATCC CCL81 or its derivatives) or bovine kidney cells such as the permanent bovine kidney cell MDBK (ATCC CCL22 or its derivatives) and on the other hand in embryonated chicken eggs (e.g. Valo hatching eggs, Lohmann). Replication in cell cultures is carried out in a manner known per se in stationary roller or carrier cultures in the form of monolayers or in suspension cultures. The growing media employed for the cells are all cell culture media known per se e.g. described in the product catalogue of Gibco BRL GmbH, Dieselstraβe 5, 76344 Eggenstein, such as, in particular, Minimal Essential Medium (MEM), which as essential constituents contains amino acids, vitamins, salts and carbohydrates, completed with buffer substances such as e.g. sodium bicarbonate ($NaHCO_3$) or hydroxyethyl-piperazine-N-2-ethanesulphonic acid (Hepes) and optionally animal sera, such as e.g. sera of cattle, horses or their foetuses. Eagles MEM having a content of $NaHCO_3$ of 0.1–5 g/l, preferably 0.5–3 g/l and also foetal calf serum in a concentration of 1–30% by volume, preferably 2–10% by volume, is particularly preferably employed.

The cells and cell lawns used for replication of the viruses are grown in a conventional manner almost to confluence or to the optimal cell density. Before their infection with viruses, the cell growth medium is preferably removed and the cells are preferably washed with virus replication medium. The virus replication medium employed are all cell culture media known per se, such as, in particular, the abovementioned MEM. Infection is then carried out using a virus suspension. In the virus suspension, the virus is diluted in the virus replication medium to a MOI (=multiplicity of infection, corresponds to the ratio of the number of infectious virus particles to the number of cells present) of 0.01–50, preferably 0.1–10.

Replication of the viruses is carried out with or without addition of animal sera. In the case where serum is employed, it is added to the replication medium in a concentration of 1–30% by volume, preferably 2–10% by volume.

Infection and virus replication are carried out at temperatures between room temperature and 40° C., preferably between 32 and 39° C., particularly preferably at 37° C. for several days, preferably up to complete destruction of the infected cells.

The virus-containing medium of the infected cells is further worked up, e.g. by removal of the cells and cell debris by means of filtration using pore sizes of e.g. 0.1–0.45 $\mu$m and/or centrifugation at up to 10,000×g.

Replication in embryonated chicken eggs is carried out in a manner known per se in the allantoic cavity of chicken hatching eggs which have been preincubated for 9–12 days, preferably 10 days, at a temperature of 37–39° C., preferably 38.5° C., and a relative humidity of 30–90%, preferably 50–60%, in a commercially available incubator, preferably a power-driven incubator.

The hatching eggs used for replication of the viruses are stored in the incubator standing vertically on the pointed end of the egg for 1–3 hours, preferably 2 hours, before inoculation and then infected with 10–200 $\mu$l, preferably 75–125 $\mu$l, of a virus suspension after preparation of the injection site. In the virus suspension, the virus is diluted to in the virus replication medium in a concentration of $10^1$–$10^7$ $TCID_{50}$/ml (50% culture-infectious dose per ml of suspension=the dilution stage at which 50% of the cell cultures employed would be infected), preferably $10^4$–$10^5$ $TCID_{50}$/ml. The virus replication medium employed are all cell culture media known per se, such as, in particular, the abovementioned MEM.

Infection and virus replication are carried out for several days, preferably 2–5 days, particularly preferably 3 days, under the incubation conditions indicated above.

The virus-containing allantoic fluid is obtained by aspiration after opening the calcareous shell and also the periostracum and the chorioallantoic membrane and can be further worked up e.g. by means of filtration using pore sizes of e.g. 0.1–0.45 $\mu$m and/or centrifugation at 10,000×g.

Virus purification or isolation is achieved by isopycnic or zonal centrifugation in e.g. sucrose density gradients. For this purpose, the virus-containing medium or the allantoic fluid is subjected after removal of the cell debris to a zonal centrifugation at 100,000×g until the virus particles are pelleted. A purer preparation of the virus particles results by zonal centrifugation in an aqueous solution having a higher density than the virus-containing medium. The aqueous solution used can be e.g. a 30–60% w/w, preferably 35–50% w/w, buffered solution of sucrose. A still higher degree of purity is achieved by centrifugation in density gradients. For this purpose, the virus purified from cells and cell debris and concentrated by means of zonal centrifugation is isolated by an isopycnic or zonal density gradient centrifugation in a density gradient of e.g. 30 to 50% w/w sucrose in buffered aqueous solution at a centrifugal acceleration of e.g. 100,000 to 150,000×g.

To obtain suitable genes which code for immunogenic proteins, the virus genome is first isolated from the purified virus particles. The native virus RNA is preferably obtained by treatment of the purified virus particles with detergent- and protease-containing aqueous solutions.

Anionic, cationic, amphoteric and non-ionic detergents are employed. Ionic detergents, preferably sodium dodecylsulphate, are preferably employed in a concentration of 0.1–10% by volume, preferably 0.5–3% by volume.

Proteases employed are those which act in the presence of detergents, such as e.g. pronase and, preferably, proteinase K. The proteases are employed in a concentration 0.01–10 mg/ml, preferably 0.05–0.5 mg/ml.

Preferably, aqueous, buffered solutions supplemented with RNase inhibitors are used.

Buffer substances used are salts of weak acids with strong bases such as e.g. tris(hydroxymethyl)-aminomethane, and salts of strong acids with weak bases such as e.g. primary phosphates or mixtures thereof. Tris(hydroxymethyl)-aminomethane is preferably used. The buffer substances are employed in concentrations which ensure a pH at which the RNA is not denatured. pHs of 6–8.5 are preferred, particularly preferably of 7–8.

RNase inhibitors used are e.g. ribonucleoside-vanadyl complexes, protein inhibitors (e.g. RNAguard®/Pharmacia) or preferably diethyl pyrocarbonate (DEPC) in concentrations of 0.01–2% by volume, preferably 0.1–0.5% by volume.

The lipophilic substances of the virus lysate are then extracted using solvents such as e.g. phenol, chloroform or mixtures thereof. Extraction is carried out in one or more stages.

The RNA is precipitated out of the remaining aqueous phase, by means of aqueous solutions containing alcohols such as e.g. ethanol or isopropanol and monovalent chloride or acetate salts such as e.g. sodium chloride, sodium acetate or potassium acetate.

The concentration of the alcohols is between 40 and 100% by volume, preferably 60 and 80% by volume and that of the chloride or acetate salts is between 0.01 and 1 mol/l, preferably 0.1 to 0.8 mol/l.

The precipitated RNA is recovered from the aqueous solution e.g. by centrifugation and dissolved again in an aqueous solution e.g. DEPC-water. This aqueous solution preferably contains buffer substances such as e.g. tris (hydroxymethyl)-aminomethane in concentrations of 1–100 mmol/l, preferably 10–50 mmol/l, possibly supplemented with ethylenediamine tetraacetate (EDTA) in concentrations of 0.1–10 mmol/l, preferably 1–10 mmol/l or dithiothreitol (DTT) in concentrations of 0.1–10 mmol/l, preferably 1–10 mmol/l.

The isolated RNA is stored at temperatures below −65° C.

Another method for RNA isolation is e.g. RNA extraction using guanidinium thiocyanate and subsequent caesium chloride density gradient centrifugation of the virus lysate.

Methods for RNA isolation are described in: J. Sambrook, E. F. Fritsch and T. Maniatis (Editor), Molecular Cloning, A Laboratory Manual, 2nd edition, Cold Spring Harbor Laboratory Press, 1989.

The identification of suitable genes is carried out using the isolated virus genome e.g. by:

a) RNA/DNA hybridization of the genome using known gene probes. Suitable gene probes used are DNA probes having nucleotide sequences of known genes for immunogens of related virus strains, such as e.g. simian virus 5 or canine parainfluenza virus 2.

b) Preparation of a complementary DNA (cDNA), cloning of the cDNA in e.g. bacterial plasmids such as e.g.

pBR322 to concentrate viral DNA and hybridization of the cloned DNA by means of known gene probes. Suitable gene probes used are DNA probes having nucleotide sequences of known genes for immunogens of related virus strains, such as e.g. simian virus 5 or canine parainfluenza virus 2.

c) Preparation of a complementary DNA (cDNA) and cloning of the cDNA in plasmid expression vectors such as e.g. pUC18/19 or pUC 118/119 or in λ-bacteriophage expression vectors such as e.g. λgt11 and its derivatives or λZAP or λORF8. The identification of the genes is carried out by detection of their expressed immunogens with the aid of antibodies which are detected directly or indirectly e.g. by means of immunofluorescence or immunoprecipitation. Suitable antibodies are those which react with immunogens of related virus strains, such as e.g. simian virus 5 or canine parainfluenza virus 2.

d) Preparation of a complementary DNA (CDNA) and cloning of the CDNA in e.g. bacterial plasmids to concentrate viral DNA. The viral DNA of the clones is sequenced and investigated for sequence homologies using known genes of related virus strains, such as e.g. simian virus 5 or canine parainfluenza virus 2.

e) Sequencing of the cDNA during its preparation and investigation for sequence homologies with known genes of related virus strains, such as e.g. simian virus 5 or canine parainfluenza virus 2.

f) Combinations of the methods a) to e).

Methods for RNA/DNA and DNA/DNA hybridization, preparation of cDNA, cloning of DNA in plasmid and bacteriophage vectors, sequencing of DNA and methods for the immunological detection of expressed immunogens are described in:

J. Sambrook, E. F. Fritsch and T. Maniatis (Editor), Molecular Cloning, A Laboratory Manual, 2nd edition, Cold Spring Harbor Laboratory Press, 1989

F. M. Ausubel, Current protocols in molecular biology 1987–1988, John Wiley & Sons, New York, 1987

A. Mayr, Virologische Arbeitsmethoden (Virological Working Methods), Volume III, Gustav Fischer Verlag, Stuttgart, 1989

Those genes are selected in which, using the above-mentioned methods, a nucleotide sequence can be detected which codes for one or more immunogens.

As example, in the sequence listing (below) are given the nucleotide sequence and the corresponding amino acid sequence of the neuraminidase-hemagglutinin- and of the fusion-protein-gene of the Parainfluenza virus type 2 deposited at CNCM under the number I-1331.

These genes, which code for one or more immunogens (foreign DNA), are inserted in a genome vector which expresses the foreign gene during the infection of a cell or of an organism. Vector viruses and vector bacteria are suitable for this purpose. For example, DNA viruses are used which have a stable genome with known insertion sites for the acceptance of 0.1 up to 20 kB (1,000 base pairs) foreign DNA, such as e.g. vaccinia viruses, herpes viruses or adenoviruses.

For this purpose it is necessary (a) first to insert the gene(s) in a shuttle vector which contains the foreign DNA flanked by DNA sequences of the vector virus. Subsequently, (β) the gene(s) is inserted in the vector virus genome e.g. by means of cotransfection of the shuttle vector and of the vector virus.

Suitable shuttle vectors are plasmid or bacteriophage vectors.

Examples of standard plasmid vectors are pBR322, pUC18/19, pAT153, pACYC184 or pSP64/65 and for bacteriophage vectors λgt10/11, λZAP or M13mp18/19.

(α) Insertion of the gene(s) into a shuttle vector

The insertion site carrying DNA fragment which carries the of the vector virus is first inserted in the shuttle vector DNA. For this purpose, both the DNA sequences of known insertion sites of the genome of the vector virus and the DNA of the shuttle vector are treated with restriction endonucleases (restriction enzymes) in order to produce ends suitable for insertion. The shuttle vector DNA prepared in such a way is mixed with an excess of the DNA fragment to be inserted, e.g. approximately in a ratio of 1:5. The DNA mixture is treated with DNA ligases in order to bind the DNA fragment covalently in the vector.

When using a shuttle plasmid, it is incorporated in pro- or eucaryotic cells, preferably bacteria, and replicated. Suitable is e.g. *Escherichia coli* K12 and its derivatives.

Bacteria which carry fragment-containing plasmids are selected.

The cloning of the insertion site in the shuttle plasmid genome, its insertion in pro- or eucaryotic cells, replication and selection of the transformed bacteria are described in detail in J. Sambrook, E. F. Fritsch and T. Maniatis (Editor), Molecular Cloning, A Laboratory Manual, 2nd edition, Cold Spring Harbor Laboratory Press, 1989 and F. M. Ausubel, Current protocols in molecular biology 1987–1988, John Wiley & Sons, New York, 1987.

If necessary, so-called “polylinkers” are inserted in the insertion sites of the vector virus. Polylinkers are DNA sequences having at least two defined restriction enzyme cleavage sites in sequence.

To do this, the insertion site carrying DNA fragment is treated with such a restriction enzyme that the fragment is only opened at one site. The fragment thus prepared is incubated together with the polylinker and DNA ligase for the specific insertion of defined restriction enzyme cleavage sites.

The polylinker can be inserted in the isolated DNA fragment or the insertion site carrying DNA fragment cloned in shuttle vectors.

If the polylinker is inserted in isolated DNA fragments, they have to be inserted in a shuttle vector. When using a shuttle plasmid, it is incorporated and replicated in pro- or eucaryotic cells, preferably bacteria. Suitable is e.g. *Escherichia coli* K12 and its derivatives. Bacteria which contain the plasmids containing DNA fragments are selected.

If the polylinker is inserted into the DNA fragment cloned in shuttle vectors, these are replicated and selected.

Genes which code for one or more immunogens (foreign DNA) are inserted in the insertion sites.

If necessary, partial sequences of the insertion site carrying the DNA fragment are previously removed. To do this, the DNA fragment is treated with restriction enzymes and the resulting DNA fragments are separated.

To insert the foreign DNA, the isolated DNA fragment or the insertion site carrying the DNA fragment cloned in shuttle vectors, is treated with one or more restriction enzymes and the fragment is opened at the insertion site or at the inserted polylinker. The foreign DNA is inserted in the insertion site prepared in this way, for example, with the aid of DNA ligases.

If the foreign DNA is inserted in isolated DNA fragments, these then have to be inserted in a shuttle vector. When using a shuttle plasmid this is incorporated in pro- or eucaryotic cells, preferably bacteria, and replicated. Suitable is e.g. *Escherichia coli* K12 and its derivatives. Bacteria which contain plasmids containing foreign DNA are selected.

If the foreign DNA is inserted in the DNA fragment cloned in shuttle vectors, these are replicated and selected.

Methods for the preparation of shuttle vectors are described in detail in J. Sambrook, E. F. Fritsch and T. Maniatis (Editor), Molecular Cloning, A Laboratory Manual, 2nd edition, Cold Spring Harbor Laboratory Press, 1989 and F. M. Ausubel, Current protocols in molecular biology 1987–1988, John Wiley & Sons, New York, 1987.

(β) Insertion of the foreign DNA in the vector virus genome

The following methods can be used for insertion of the foreign DNA in the vector virus genome (i) Cotransfection of suitable cells with the shuttle vector DNA and the isolated, native vector virus DNA, (ii) Transfection of suitable cells with the shuttle vector DNA and infection with the vector virus, (iii) Infection of suitable cells with the vector virus and transfection with the shuttle vector DNA.

Methods suitable for this purpose are described in detail in J. Sambrook, E. F. Fritsch and T. Maniatis (Editor), Molecular Cloning, A Laboratory Manual, 2nd edition, Cold Spring Harbor Laboratory Press, 1989 and F. M. Ausubel, Current protocols in molecular biology 1987–1988, John Wiley & Sons, New York, 1987.

The method (i), which is carried out in the form of the calcium phosphate DNA precipitation technique, is preferably employed. To this end, the following steps are necessary:

(1) The shuttle vector is replicated, isolated and further purified. Purification of the shuttle vector DNA is carried out e.g. by means of isopycnic density gradient centrifugation, e.g. in a caesium chloride density gradient.

The vector virus is replicated and purified. The viral genome is isolated and further purified. Purification of the vector virus DNA is carried out e.g. by means of isopycnic density gradient centrifugation, e.g. in a caesium chloride density gradient.

(2) For cotransfection, circular or preferably linearized shuttle vector DNA is used.

The linearized shuttle vector DNA is obtained e.g. by treatment of the purified DNA with restriction enzymes. Restriction enzymes are preferred which have no recognition site in the inserted foreign DNA, i.e. the foreign DNA sequence is not divided.

(3) The vector virus DNA and the shuttle vector DNA are mixed e.g. in a ratio of 0.01 to $0.1 \times 10^{-12}$ mol/l of vector virus DNA to 1 to $3 \times 10^{-12}$ mol/l of shuttle vector DNA.

(4) The DNA mixture is coprecipitated with e.g. calcium phosphate and transferred to suitable cells.

Suitable cells are animal cells, in particular permanent cell lines, such as e.g. the porcine kidney cell PK15 (ATCC CCL33 or its derivatives), the monkey kidney cell BGM (Flow 03-240 or its derivatives) or Vero (ATCC CCL81 or its derivatives), the bovine kidney cell MDBK (ATCC CCL22 or its derivatives), the canine kidney cell MDCK (ATCC CCL34 or its derivatives) or the rabbit kidney cell RK-13 (ATCC CCL37).

Cotransfection can also be carried out by means of other methods. Those which may be mentioned are e.g. the DEAE/dextran method, the liposome method or electroporation.

(5) The cells are cultured, e.g. according to the methods described further above. If a cythopatho-genetic effect occurs, clones of the vector virus are isolated by means of the individual plaque purification methods and further replicated.

Methods for individual plaque purification are described in A. Mayr, Virologische Arbeitsmethoden [Virological Working Methods], Volume I, Gustav Fischer Verlag, Stuttgart, 1974.

(6) The selection of recombinant vector viruses is carried out (i) by detection of the expression of the foreign gene or (ii) by detection of the inserted foreign DNA in the vector virus genome e.g. by DNA/DNA hybridization.

(i)

Detection of the expression of the foreign DNA is carried out, for example, with the aid of antibodies. Suitable antibodies are those which react with immunogens of related virus strains, such as e.g. simian virus 5 or canine parainfluenza virus 2. The gene product of the foreign DNA can be detected e.g. by means of immunofluorescence or immunoprecipitation.

(ii)

Detection of the inserted foreign DNA is carried out by hybridization with gene probes of the corresponding foreign gene.

Stable recombinant vector viruses are replicated in known, conventional processes, such as described further above, isolated and further worked up used as antigenic material.

In the vaccines according to the invention, the antigenic material is present on its own or in formulations. Ingredients of those formulations which may be mentioned are pharmacologically tolerable solvents or diluents, adjuvants, preservatives, and suspension promoters or solubilizers such as emulsifiers.

The antigenic material is employed as a biologically active substance in the formulation of vaccines.

To prepare a live vaccine, the antigenic material is used in the form of live virus particles, to which additives and optionally also antifoams and preservatives are added for stabilization. To improve storage ability, the live vaccine is freeze-dried. Before use of this vaccine the lyophilized product is reconstituted with a solvent, such as e.g. aqua dest., aqua purificata or 0.9% saline solution.

The virus particles purified from the cell substrate are mixed in a concentration of at least $10^6$ $CID_{50}$/ml together with protective colloids or stabilizers, such as e.g. celluloses, dextrans, gelatins, collidones or stearates and optionally supplemented with antifoams, such as e.g. tributyl phosphate, isopropanol or silicone oil and also preservatives, such as e.g. merthiolate or thimerosal in an aqueous pH-buffered solution, filled into appropriate containers and freeze-dried.

To prepare inactivated vaccines, the antigenic material used is complete, killed virus particles in a concentration of $10^{4.0}$–$10^{9.0}$ $CID_{50}$/ml, preferably $10^{5.0}$–$10^{8.0}$ $CID_{50}$/ml before inactivation or fragments (subunits) of the virus particles in a concentration that 10–250 mg of protein, preferably 10–100 mg of protein, are contained per vaccine dose. The antigenic material is present in the vaccine in a formulation using substances such as solvents and diluents, adjuvants, preservatives, suspension promoters or solubilizers, pH-regulating agents and optionally antifoams.

Solvents and diluents which may be mentioned are aqua dest., aqua purificata, physiologically tolerable saline solutions and cell culture media. In particular, the abovementioned E-MEM and phosphate-buffered saline solution (PBS) are used.

Adjuvants which may be mentioned are:

1.) Mineral salts such as aluminium hydroxide, aluminium phosphate, calcium phosphate, kaolin or silicon. 10–50% by volume, preferably 25–35% by volume, of an aluminium hydroxide gel having a content of 1–5% (w/v), preferably 2–3% (w/v), of aluminium hydroxide are preferably employed.

2.) Oily adjuvants such as non-toxic mineral oils (e.g. Draceol®, liquid paraffin), vegetable oils (e.g. lecithins, groundnut oils) or animal oils (squalanes, squalenes), which are employed in a concentration 1–40% by volume, preferably 1–15% by volume.

3.) Hydrophilic and hydrophobic polymers such as polyoxyethylene and polyoxypropylene. Synthetically prepared block copolymers (e.g. Pluronic® L101, Pluronic® L121, Pluronic® L122, Tetronic® 1501) in a concentration of 1–10% by volume are preferably employed.

4.) Adjuvants of bacterial origin such as pertussis toxin (Bordatella pertussis), Salmonella typhimurium mitogen or bacterial endotoxins such as lipopolysaccharides (LPS, e.g. from mycobacteria or salmonellae) and also LPS analogues or derivates such as e.g. lipid A, monophosphoryl lipid A (MPL), diphosphoryl lipid A, (DPL), trehalose dimycolate (TDM), muramyl dipeptide (MDP) or adamantyl dipeptide (AdDP) and their derivatives. MDP derivatives or AdDP in a concentration of 0.0001–10% (w/v) are preferably employed.

5.) Organic water-dispersible adjuvants such as cholesterol, gelatin, phosphatidylcholine, polysaccharides (e.g. zymosan, agar), aliphatic amines (e.g. dimethyldioctadecylamine/DDA, N,N.diotadecyl-N', N'-bis(2-hydroxyethyl)propanediamine/Avridin®), DEAE-dextrans or saponin (from the bark of Quillaja saponaria Molina) and saponin derivates (Quil A).

6.) Monokines and lymphokines, such as e.g. interleukin-1, interleukin-2 or γ-interferon.

7.) Possible combinations of 1.) to 6.)

Preservatives which may be mentioned are formalin in concentrations up to 1%, phenol and benzyl alcohol in concentrations up to 0.5%, sorbic acid, benzoic acid, sodium benzoate, and their derivatives such as e.g. the sodium salt of 2-(ethylmercurio-thio)-benzoic acid (merthiolate, thimerosal, thiomersal) or the sodium salt of 4-(ethylmercurio-thio)-benzenesulphonic acid (thiomerfonate). Merthiolate is preferably employed in concentrations of 0.01% to 0.5%.

Suspension promoters and solubilizers which may be mentioned are non-toxic surface-active substances such as vegetable proteins, alginates, celluloses, phospholipids and in particular substances based on glycol ethers such as polyethylene glycols and their derivatives. Polyethylene glycol (PEG) 200, 300, 400, 600 and 900 and PEG derivatives (Span®, Arlacel®, Tween®, Myri®, Brij®) are preferably employed, particularly preferably Tween® 80 in a concentration of 0.05–5% by volume, preferably 0.2–1% by volume.

pH-regulating substances which may be mentioned are e.g. sodium hydroxide and potassium hydroxide, sodium carbonate and potassium carbonate, acetic, tartaric and citric acid or hydroxyethylpiperazine-N-2-ethanesulphonic acid (HEPES).

Antifoams which may be mentioned are tributyl phosphate, isopropanol, silicone oil, Antifoam® or Baysilon® antifoamer EBZ.

Parainfluenza viruses according to the invention which can cause diseases of the respiratory and reproductive tract of pigs are obtained e.g. as follows:

Organs are removed from diseased pigs showing PRRS-like symptomatology and subjected to a virus isolation. Weak or ill piglets from infected stocks are particularly suitable. The internal organs, in particular the lungs, liver, kidneys and spleen are removed from a suitable animal. Parts of these organs or organ mixtures are homogenized in physiologically tolerable aqueous solutions to give suspensions, the proportion of organs amounting to about 10% (w/v). A particularly suitable solution is the Eagles Minimum Essential Medium (E-MEM) described above. The suspensions are purified from cells and cell debris by centrifugation at about 1500×g. A further purification of the centrifugation supernatant can be carried out by filtering. Suitable filters having a pore size of 0.2–5 μm, preferably 0.2–0.45 μm.

From the organs, preferably the lungs, a primary cell culture can also be made which is investigated for the occurrence of cythopathogenic effects (CPE). To do this, the chopped tissue is subjected to an enzymatic by proteases. Trypsin in a concentration of 0.1–0.5% (w/v), preferably 0.125–0.25% (w/v) in a physiological, aqueous solution is particularly suitable for this purpose. The trypsin digestion is carried out at 20–37° C., preferably at room temperature, in the course of 2–8 hours. Undigested tissue are separated by pieces of coarse filtration. The trypsinized cells are recovered by centrifugation at 500–1500×g. The cell sediment is resuspended in a suitable growth medium, such as e.g. the E-MEM described, and inoculated into culture vessels in a concentration of $10^5$–$10^6$ cells/ml of medium. Depending on the growth rate, the growth medium is exchanged every 3–7 days. The growth of the cells and the occurrence of a CPE is observed daily. The cell culture supernatant may additionally be checked for haemagglutinating properties at fixed time intervals of 2–7 days.

The centrifugation supernatants or filtrates of the organ homogenates and the cell culture supernatants of the primary organ cultures are applied in a dilution of 1:1 to 1:1000, preferably 1:10 to 1:100, to primary or permanent mammalian cell cultures and incubated at 32–39° C., preferably 37° C., for several days. Cell lawns are used for this purpose which are grown to 20–100%, preferably 80–100%, confluence. The cell cultures are checked daily for the occurrence of a CPE. The cell culture supernatant may additionally be checked for haemagglutinating properties at fixed intervals of 2–7 days. If no signs of virus replication occur, the cell culture supernatants are passaged further in the dilutions mentioned on fresh cell cultures. This process can be repeated two or more times.

If signs of virus replication occur, the virus is adapted to the cell culture used by further passages.

An unborn piglet was removed from the uterus of an aborting sow which originated from a herd with PRRS-like symptomatology. From a primary lung cell culture and by subsequent passaging of the culture supernatant cell lines it was possible to isolate a cythopathogenic agent from the lungs of this piglet. It was characterized as an enveloped haemagglutinating single-stranded RNA virus of about 200 nm in diameter, which showed by electron microscopic examinations the morphology of a paramyxovirus. Proteins of this virus were detected in its Western Blots an antiserum against a parainfluenza virus type 2 (Pl-2). In the same test system, an antiserum prepared against the isolated virus detected Pl-2 strain "SV5", by which the serological relationship of the isolated virus to parainfluenza virus type 2 is confirmed.

This parainfluenza isolate with the notation "SER" was deposited on Dec. 6, 1993 in the "Collection Nationale de Cultures et de Microorganismes" of the "Institut Pasteur", Paris, France under the number I-1331.

The isolated virus can be replicated on a large scale using animal cell cultures. Purified antigen preparations can be prepared from virus suspensions produced in this way by means of suitable technical processes (centrifugation, tangential filtration). These can be used as starting material for the diagnosis and for the prevention of respiratory and reproductive diseases of the pig, in particular PRRS.

EXAMPLE 1

Isolation of the parainfluenza isolate "SER"

It was possible to isolate the parainfluenza isolate "SER" from the lungs of a piglet which had been removed from the uterus by section of an aborting sow originating from a herd showing PRRS-like symptomatology, which had been euthanized.

PK15 cells (cloned porcine kidney cell, ATCC No. CCL 33)
Eagles Minimum Essential Medium containing Earl's salts (E-MEM):

| | |
|---|---|
| E-MEM - powder containing Phenol Red (e.g. Gibco BRL 072-0110) | for 100 l |
| Non-essential amino acids, stock solution 100× | 1000 ml |
| Neomycin sulphate | 3 g |
| Polymyxin B sulphate | 3 MU |
| Aqua purificata (EP 8) | to 100 l |

Non-essential amino acids, stock solution 100×:

| | |
|---|---|
| Alanine (EP 752) | 8.9 g |
| Asparagine monohydrate (GP 10) | 15.0 g |
| L-Aspartic acid | 13.2 g |
| Glycine (EP 614) | 7.5 g |
| Glutamic acid (EP 750) | 14.7 g |
| Proline (EP 785) | 11.5 g |
| Serine (EP 788) | 10.5 g |
| Aqua purificata (EP 8) | to 10 l |

Foetal calf serum (FCS, e.g. Gibco BRL 012-06290)
Growth medium: E-MEM containing 2.0 g/l of sodium bicarbonate and 2% FCS
Maintenance medium: E-MEM containing 0.85 g/l of sodium bicarbonate and 5% FCS
0.25% trypsin solution (e.g. Gibco BRL 043-05050)
PBS buffer (Phosphate Buffered Saline):

| | |
|---|---|
| NaCl | 8.0 g |
| KCl | 0.2 g |
| $KH_2PO_4$ | 0.2 g |
| $Na_2HPO_4 \times 12 H_2O$ | 2.9 g |
| Aqua purificata (EP 8) | to 1000 ml |

Tissue culture flask, 80 cm² (Roux flask, e.g. Greiner 658 170)

A part of the piglet lung removed under sterile conditions was chopped using scissors and subjected to an enzymatic digestion in 0.25% trypsin solution. The trypsinization was carried out with stirring at room temperature for 4 hours. Undigested large pieces of tissue were separated in a sterile gauze filter. The filtrate was washed three times in PBS by low-speed centrifugation (1000×g, 10 minutes). The cells were inoculated in 80 cm² culture flasks in E-MEM and addition of 5% FCS in a concentration of $10^5$ cells/ml and incubated at 37° C. The growth medium was changed every 4–5 days. The growth of the primary culture was observed daily by microscopic examination. Attention was paid in particular to the occurrence of cytopathogenic effects (CPE). After about 2 weeks, a CPE in the form of rounding, shrinking cells having a slow tendency to spread could be observed. The culture supernatant of the primary cells was diluted 1:10 with maintenance medium and inoculated onto confluent monolayers of PK-15 cell cultures in 80 cm² culture flasks (incubation volume: 40 ml). A non-infected culture of each cell was additionally carried out as a control. After incubation for 7 days, a CPE develops with beginning destruction of the monolayer. The culture was subjected to a freeze-thaw process and the supernatant was diluted 1:10 inoculated onto a fresh culture whose supernatant was tested after 6–7 days in the haemagglutination test using chicken erythrocytes. In the 4th passage, the cultures after incubation for 6 days exhibited a cytopathogenic effect to approximately 100%. Culture supernatants which were positive in the haemagglutination test were stored at −70°C.

EXAMPLE 2

Replication of the parainfluenza isolate "SER"
Material

Parainfluenza isolate "SER", masterseed
PK-15 cells (cloned porcine kidney cell, ATCC No. CCL 33)
Eagles Minimum Essential Medium containing Earle's salts (E-MEM):

| | |
|---|---|
| E-MEM - powder containing Phenol Red (e.g. Gibco BRL 072-0110) | for 100 l |
| Non-essential amino acids, stock solution 100× | 1000 ml |
| Neomycin sulphate | 3 g |
| Polymyxin B sulphate | 3 MU |
| Aqua purificata (EP 8) | to 100 l |

Foetal calf serum (FCS, e.g. Gibco BRL 012-06290)
Growth medium: E-MEM containing 2.0 g/l of sodium bicarbonate and 2% FCS
Maintenance medium: E-MEM containing 0.85 g/l of sodium bicarbonate and 5% FCS
Tissue culture flask, 80 cm² (Roux flask, e.g. Greiner 658 170)
multi tray-disk, 6,000 cm² (e.g. Nunc 164 327)

Methodology

The growth medium of a tissue culture flask grown to confluence with PK-15 cells is discarded and the latter covered with 40 ml of the virus masterseed diluted 1:50 in maintenance medium. After incubation for 7 days at 37° C., the contents of the tissue culture flask, subjected to a freeze-thaw process and suspended by ultrasound, are made up to a volume of 3,000 ml with maintenance medium and herewith a multi tray-disk grown to confluence with PK-15 cells is inoculated. After incubation at 37° C. for 7 days, the culture supernatant is harvested and stored at −70° C. until further processing.

EXAMPLE 3

Production of inactivated vaccine (parainfluenza isolate "SER")
Material

Parainfluenza isolate "SER", cell culture supernatant from virus replication(s)
2-Bromoethylamine hydrobromide (2-BEA) solution: 0.5 M stock

| | |
|---|---|
| 2-Bromoethylamine hydrobromide (2-BEA, $BrCH_2CH_2NH_2HBr$, Merck 820176) | 102.5 g |
| Aqua purificata (EP 8) | to 1000 ml |

Sodium thiosulphate 2.5 M stock solution:

| | |
|---|---|
| $Na_2S_2O_3 \times 5H_2O$ (EP 414) | 620.5 g |
| Aqua purificata (EP 8) | to 1000 ml |

Aluminium hydroxide suspension 3% (e.g. Superfos)
Quil A 1% stock solution

| | |
|---|---|
| Quil A (e.g. Superfos) | 10.0 g |
| Aqua purificata (EP 8) | to 1000 ml |

Thimerosal 2% stock solution

| | |
|---|---|
| Thimerosal ($C_9H_9HgNaO_2S$) | 50.0 g |
| Aqua purificata (EP 8) | to 1000 ml |

-continued

PBS buffer (Phosphate Buffered Saline):

| | |
|---|---|
| NaCl | 8.0 g |
| KCl | 0.2 g |
| KH$_2$PO$_4$ | 0.2 g |
| Na$_2$HPO$_4$ × 12 H$_2$O | 2.9 g |
| Aqua purificata (EP 8) | to 1000 ml |

The supernatant of the virus replicated in cell cultures is purified from cells and cell debris by centrifugation at 10,000×g. A virus suspension purified in such a way with a concentration of virus particles of $10^{6.0}$ CID$_{50}$/ml, which originates from one or more virus harvests, is transferred to a sterile vessel. The pH is adjusted to 8.4 using sodium hydroxide solution (2N NaOH). Such an amount of 0.5M 2-bromoethylamine hydrobromide solution (2-BEA) is added with continuous stirring until a final concentration of 5 mmol/l of 2-BEA is achieved. Inactivation of the virus is carried out in the course of 18 hours at 37° C. The inactivating agent is then neutralized at 4° C. by addition of a 2.5M sodium thiosulphate solution up to a final concentration of 50 mmol/l.

62 ml of the inactivated virus suspension are added to 31 ml of a sterile aluminium hydroxide suspension (3% Al(OH)$_3$, pH 7.3) and the mixture is stirred at 4° C. for 2 hours. After addition of 1.25 ml of Quil A (2% solution) and 0.1 ml of thimerosal (2% solution), the mixture is filled up to 100 ml with PBS buffer and stirred at 4° C. for a further 20 hours. The finished vaccine is filled into multiple-dose containers and stored at 4° C.

Inoculation of pigs of all age groups is carried out by subcutaneous administration of 2 ml of this vaccine.

Publications containing published nucleotide sequences which code for immunogens of simian virus 5

Hiebert, S. W., Paterson, R. G. & Lamb, R. A. (1985). Hemagglutinin-neuraminidase protein of the paramyxovirus simian virus 5: nucleotide sequence of the mRNA predicts a N-terminal membrane anchor. Journal of Virology, 54, 1–6.

Hiebert, S. W., Paterson, R. G. & Lamb, R. A. (1985). Identification and predicted sequence of a previously unrecognized small hydrophobic protein, SH, of the paramyxovirus simian virus 5. Journal of Virology, 55, 744–751.

Paterson, R. G., Harris, T. J. R. & Lamb, R. A. (1984). Analysis and gene assignment of mRNAs of a paramyxovirus, simian virus 5. Virology, 138, 310–323.

Paterson, R. G., Harris, T. J. R. & Lamb, R. A. (1984). Fusion protein of the paramyxovirus simian virus 5: nucleotide sequence of mRNA predicts a highly hydrophobic glycoprotein. Proc. Natl. Acad. Sci. USA, 81, 6706–6710.

Paterson, R. G., Hiebert, S. W. & Lamb, R. A. (1985). Expression at the cell surface of biologically active fusion and hemagglutinin/neuraminidase proteins of the paramyxovirus simian virus 5 from cloned cDNA. Proc. Natl. Acad. Sci. USA, 82, 7520–7524.

Thomas, S., Lamb, R. A. & Paterson, R. G. (1988). Two mRNAs that differ by two nontemplated nucleotides encode the amino coterminal proteins P and V of the paramyxovirus SV5. Cell, 54, 891–902.

We claim:

1. Antigenic material comprising isolated whole particles or subunits of a porcine parainfluenza virus type 2.

2. The porcine parainfluenza virus type 2 according to claim 1 having Accession No. I-1331.

3. The antigenic material according to claim 1 further comprising antigenic material selected from the group consisting of *Chlamydia psitaci*, *Chlamydia pecorum* and *Erysipelothrix thusiopathiae*.

4. A composition for immunizing pigs against a porcine parainfluenza virus causing disease of the respiratory or reproductive tract, comprising an immunogenically effective amount of antigenic material according to claim 1 in living, killed, or attenuated form.

5. A method of immunizing pigs against diseases of the respiratory or reproductive tract comprising administering to said pigs an effective amount therefor of a composition according to claim 4.

6. A process for preparing antigenic material according to claim 1 comprising replicating porcine parainfluenza virus type 2 to yield a virus suspension and thereafter isolating the antigenic material from said virus suspension.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1698 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: CDS
      (B) LOCATION:1..1695

(xi) SEQUENCE DESCRIPTION: SEQ ID NO: 1:

```
ATG GTT GCA GAA GAT GCC CCT GTT AGG GGC ACT TGC CGA GTA TTA TTT      48
Met Val Ala Glu Asp Ala Pro Val Arg Gly Thr Cys Arg Val Leu Phe
 1               5                  10                  15

CGA ACA ACA ACT TTA ATT TTT CTA TGC ACA CTA CTA GCA TTA AGC ATC      96
Arg Thr Thr Thr Leu Ile Phe Leu Cys Thr Leu Leu Ala Leu Ser Ile
                20                  25                  30

TCT ATC CTT TAT GAG AGT TTA ATA ACC CAA AAG CAA ATC ATG AGC CAC     144
Ser Ile Leu Tyr Glu Ser Leu Ile Thr Gln Lys Gln Ile Met Ser His
         35                  40                  45

GCA GGA TAC ACT CGA TCT AAT TCT AGA TTA GGA AGT ATC ACT GAT CTT     192
Ala Gly Tyr Thr Arg Ser Asn Ser Arg Leu Gly Ser Ile Thr Asp Leu
 50                  55                  60
```

| | | |
|---|---|---|
| CTT AAT AAT ATT CTC TCT GTC GCA AAT CAG ATT ATA TAT AAC TCT GCA<br>Leu Asn Asn Ile Leu Ser Val Ala Asn Gln Ile Ile Tyr Asn Ser Ala<br>65                  70               75              80 | 240 |
| GTC GCT CTA CCT CTA CAA TTG GAC ACT CTT GAA TCA ACA CTC CTT ACA<br>Val Ala Leu Pro Leu Gln Leu Asp Thr Leu Glu Ser Thr Leu Leu Thr<br>                 85              90              95 | 288 |
| GCC ATT AAG TCT CTT CAA ACC AGT GAC AAG CTA GAA CAG AAC TGC TCG<br>Ala Ile Lys Ser Leu Gln Thr Ser Asp Lys Leu Glu Gln Asn Cys Ser<br>           100               105            110 | 336 |
| TGG GGT GCT GCA CTG ATT AAT AAT AAT AGA TAC ATT AAT GGC ATC AAT<br>Trp Gly Ala Ala Leu Ile Asn Asn Asn Arg Tyr Ile Asn Gly Ile Asn<br>      115                 120              125 | 384 |
| CAG TTC TAT TTT TCA ATT GCT GAG GGT CGC AAT CTG ACA CTT GGC CCA<br>Gln Phe Tyr Phe Ser Ile Ala Glu Gly Arg Asn Leu Thr Leu Gly Pro<br>130                 135              140 | 432 |
| CTT CTT AAT ATA CCT AGT TTC ATT CCA ACT GCC ACG ACA CCA GAG GGC<br>Leu Leu Asn Ile Pro Ser Phe Ile Pro Thr Ala Thr Thr Pro Glu Gly<br>145                 150              155            160 | 480 |
| TGC ACC AGG ATC CCA TCA TTC TCG CTC ACC AAG ACA CAC TGG TGT TAT<br>Cys Thr Arg Ile Pro Ser Phe Ser Leu Thr Lys Thr His Trp Cys Tyr<br>                 165              170            175 | 528 |
| ACA CAC AAT GTT ATC CTG AAT GGA TGC CAG GAT CAT GTA TCC TCA AAT<br>Thr His Asn Val Ile Leu Asn Gly Cys Gln Asp His Val Ser Ser Asn<br>          180               185            190 | 576 |
| CAA TTT GTT TCC ATG GGA ATC ATT GAA CCC ACT TCT GCC GGG TTT CCA<br>Gln Phe Val Ser Met Gly Ile Ile Glu Pro Thr Ser Ala Gly Phe Pro<br>                 195              200            205 | 624 |
| TCC TTT CGA ACC CTA AAG ACT CTA TAT CTC AGC GAT GGG GTC AAT CGT<br>Ser Phe Arg Thr Leu Lys Thr Leu Tyr Leu Ser Asp Gly Val Asn Arg<br>      210               215              220 | 672 |
| AAG AGC TGC TCT ATC AGT ACA GTT CCG GGG GGT TGT ATG ATG TAC TGT<br>Lys Ser Cys Ser Ile Ser Thr Val Pro Gly Gly Cys Met Met Tyr Cys<br>225                 230              235            240 | 720 |
| TTT GTC TCT ACT CAA CCA GAG AGG GAT GAC TAC TTT TCT ACC GCT CCT<br>Phe Val Ser Thr Gln Pro Glu Arg Asp Asp Tyr Phe Ser Thr Ala Pro<br>                 245              250            255 | 768 |
| CCA GAA CAA CGA ATT ATT ATA ATG TAC TAT AAT GAT ACA ATC GTG GAG<br>Pro Glu Gln Arg Ile Ile Ile Met Tyr Tyr Asn Asp Thr Ile Val Glu<br>                 260              265            270 | 816 |
| CGC ATA ATT AAT CCA CCC GGG GTA CTA GAT GTA TGG GCA ACA TTG ACC<br>Arg Ile Ile Asn Pro Pro Gly Val Leu Asp Val Trp Ala Thr Leu Thr<br>             275              280            285 | 864 |
| CCA GGA ACA GGA AGC GGG GTA TAT TAT TTA GGT TGG GTG CTC TTT CCA<br>Pro Gly Thr Gly Ser Gly Val Tyr Tyr Leu Gly Trp Val Leu Phe Pro<br>      290               295              300 | 912 |
| ATA TAT GGC GGC GTG ATT AAA GAT ACG AGT TTA TGG AAT AAT CAA GCA<br>Ile Tyr Gly Gly Val Ile Lys Asp Thr Ser Leu Trp Asn Asn Gln Ala<br>305                 310              315            320 | 960 |
| AAT AAA TAC TTT ATC CCC CAG ATG GTT GCT GCT CTC TGC TCA CAA AAC<br>Asn Lys Tyr Phe Ile Pro Gln Met Val Ala Ala Leu Cys Ser Gln Asn<br>                 325              330            335 | 1008 |
| CAG GCA ACT CAA GTC CAA AAT GCT AAG TCA TCA TAC TAT AGC AGC TGG<br>Gln Ala Thr Gln Val Gln Asn Ala Lys Ser Ser Tyr Tyr Ser Ser Trp<br>             340              345            350 | 1056 |
| TTT GGC AAT CGA ATG ATT CAG TCT GGG ATC CTG GCA TGT CCT CTT CAA<br>Phe Gly Asn Arg Met Ile Gln Ser Gly Ile Leu Ala Cys Pro Leu Gln<br>      355               360              365 | 1104 |
| CAG GAT CTA ACC AAT GAG TGT TTA GTT CTG CCC TTT TCT AAT GAT CAG<br>Gln Asp Leu Thr Asn Glu Cys Leu Val Leu Pro Phe Ser Asn Asp Gln<br>370                 375              380 | 1152 |

-continued

```
GTG CTT ATG GGT GCT GAA GGG AGA TTA TAC ATG TAT GGT GAC TCG GTG    1200
Val Leu Met Gly Ala Glu Gly Arg Leu Tyr Met Tyr Gly Asp Ser Val
385                 390                 395                 400

TAT TAC TAC CAA AGA AGC AAT AGT TGG TGG CCT ATG ACC ATG CTG TAT    1248
Tyr Tyr Tyr Gln Arg Ser Asn Ser Trp Trp Pro Met Thr Met Leu Tyr
                405                 410                 415

AAG GTA ACC ATA ACA TTC ACT AAT GGT CAG CCA TCT GCT ATA TCA GCT    1296
Lys Val Thr Ile Thr Phe Thr Asn Gly Gln Pro Ser Ala Ile Ser Ala
            420                 425                 430

CAG AAT GTG CCC ACA CAG CAG GTC CCT AGA CCT GGG ACA GGA GCC TGC    1344
Gln Asn Val Pro Thr Gln Gln Val Pro Arg Pro Gly Thr Gly Ala Cys
                435                 440                 445

TCT GCA ACA AAT AGA TGT CCC GGT TTT TGC TTG AAA GGA GTG TAT GCT    1392
Ser Ala Thr Asn Arg Cys Pro Gly Phe Cys Leu Lys Gly Val Tyr Ala
450                 455                 460

GAT GCC TGG TTA CTG ACC AAC CCT TCG TCT ACC AGT ACA TTT GGA TCA    1440
Asp Ala Trp Leu Leu Thr Asn Pro Ser Ser Thr Ser Thr Phe Gly Ser
465                 470                 475                 480

GAA GCA ACC TTC ACT GGT TCT TAT CTC AAC GCA GCA ACT CAG CGT ATC    1488
Glu Ala Thr Phe Thr Gly Ser Tyr Leu Asn Ala Ala Thr Gln Arg Ile
                485                 490                 495

AAT CCG ACG ATG TAT ATC GCG AAC AAC ACA CAG ATC ATA AGC TCA CAG    1536
Asn Pro Thr Met Tyr Ile Ala Asn Asn Thr Gln Ile Ile Ser Ser Gln
                500                 505                 510

CAA TTT GGA TCA AGC GGT CAA GAA GCA GCA TAT AGC CAC ACA ACT TGT    1584
Gln Phe Gly Ser Ser Gly Gln Glu Ala Ala Tyr Ser His Thr Thr Cys
            515                 520                 525

TTT AGG GAC ACA GGC TCT GTT ATG GTA TAC TGT CTC TAT ATT ATT GAA    1632
Phe Arg Asp Thr Gly Ser Val Met Val Tyr Cys Leu Tyr Ile Ile Glu
530                 535                 540

TTG TCC TCA TCT CTC TTA GGA CAA TTT CAG ATT GTC CCA TTT ATC CGT    1680
Leu Ser Ser Ser Leu Leu Gly Gln Phe Gln Ile Val Pro Phe Ile Arg
545                 550                 555                 560

CAG GTG ACA CTA TCC TAA                                             1698
Gln Val Thr Leu Ser
                565
```

(2) INFORMATION FOR SEQ ID NO: 2:

(i) SEQUENCE CHARACTERISTICS:
        (A) LENGTH: 565 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Val Ala Glu Asp Ala Pro Val Arg Gly Thr Cys Arg Val Leu Phe
1               5                   10                  15

Arg Thr Thr Thr Leu Ile Phe Leu Cys Thr Leu Leu Ala Leu Ser Ile
                20                  25                  30

Ser Ile Leu Tyr Glu Ser Leu Ile Thr Gln Lys Gln Ile Met Ser His
            35                  40                  45

Ala Gly Tyr Thr Arg Ser Asn Ser Arg Leu Gly Ser Ile Thr Asp Leu
        50                  55                  60

Leu Asn Asn Ile Leu Ser Val Ala Asn Gln Ile Ile Tyr Asn Ser Ala
65                  70                  75                  80

Val Ala Leu Pro Leu Gln Leu Asp Thr Leu Glu Ser Thr Leu Leu Thr
                85                  90                  95

Ala Ile Lys Ser Leu Gln Thr Ser Asp Lys Leu Glu Gln Asn Cys Ser
                100                 105                 110
```

-continued

```
Trp Gly Ala Ala Leu Ile Asn Asn Asn Arg Tyr Ile Asn Gly Ile Asn
    115                 120                 125
Gln Phe Tyr Phe Ser Ile Ala Glu Gly Arg Asn Leu Thr Leu Gly Pro
    130                 135                 140
Leu Leu Asn Ile Pro Ser Phe Ile Pro Thr Ala Thr Thr Pro Glu Gly
145                 150                 155                 160
Cys Thr Arg Ile Pro Ser Phe Ser Leu Thr Lys Thr His Trp Cys Tyr
                165                 170                 175
Thr His Asn Val Ile Leu Asn Gly Cys Gln Asp His Val Ser Ser Asn
                180                 185                 190
Gln Phe Val Ser Met Gly Ile Ile Glu Pro Thr Ser Ala Gly Phe Pro
            195                 200                 205
Ser Phe Arg Thr Leu Lys Thr Leu Tyr Leu Ser Asp Gly Val Asn Arg
        210                 215                 220
Lys Ser Cys Ser Ile Ser Thr Val Pro Gly Gly Cys Met Met Tyr Cys
225                 230                 235                 240
Phe Val Ser Thr Gln Pro Glu Arg Asp Asp Tyr Phe Ser Thr Ala Pro
                245                 250                 255
Pro Glu Gln Arg Ile Ile Ile Met Tyr Tyr Asn Asp Thr Ile Val Glu
                260                 265                 270
Arg Ile Ile Asn Pro Pro Gly Val Leu Asp Val Trp Ala Thr Leu Thr
            275                 280                 285
Pro Gly Thr Gly Ser Gly Val Tyr Tyr Leu Gly Trp Val Leu Phe Pro
        290                 295                 300
Ile Tyr Gly Gly Val Ile Lys Asp Thr Ser Leu Trp Asn Asn Gln Ala
305                 310                 315                 320
Asn Lys Tyr Phe Ile Pro Gln Met Val Ala Ala Leu Cys Ser Gln Asn
                325                 330                 335
Gln Ala Thr Gln Val Gln Asn Ala Lys Ser Ser Tyr Tyr Ser Ser Trp
            340                 345                 350
Phe Gly Asn Arg Met Ile Gln Ser Gly Ile Leu Ala Cys Pro Leu Gln
        355                 360                 365
Gln Asp Leu Thr Asn Glu Cys Leu Val Leu Pro Phe Ser Asn Asp Gln
    370                 375                 380
Val Leu Met Gly Ala Glu Gly Arg Leu Tyr Met Tyr Gly Asp Ser Val
385                 390                 395                 400
Tyr Tyr Tyr Gln Arg Ser Asn Ser Trp Trp Pro Met Thr Met Leu Tyr
                405                 410                 415
Lys Val Thr Ile Thr Phe Thr Asn Gly Gln Pro Ser Ala Ile Ser Ala
            420                 425                 430
Gln Asn Val Pro Thr Gln Gln Val Pro Arg Pro Gly Thr Gly Ala Cys
        435                 440                 445
Ser Ala Thr Asn Arg Cys Pro Gly Phe Cys Leu Lys Gly Val Tyr Ala
    450                 455                 460
Asp Ala Trp Leu Leu Thr Asn Pro Ser Ser Thr Phe Gly Ser
465                 470                 475                 480
Glu Ala Thr Phe Thr Gly Ser Tyr Leu Asn Ala Ala Thr Gln Arg Ile
                485                 490                 495
Asn Pro Thr Met Tyr Ile Ala Asn Asn Thr Gln Ile Ile Ser Ser Gln
            500                 505                 510
Gln Phe Gly Ser Ser Gly Gln Glu Ala Ala Tyr Ser His Thr Thr Cys
        515                 520                 525
Phe Arg Asp Thr Gly Ser Val Met Val Tyr Cys Leu Tyr Ile Ile Glu
```

```
                    530                 535                 540
Leu Ser Ser Ser Leu Leu Gly Gln Phe Gln Ile Val Pro Phe Ile Arg
545                 550                 555                 560

Gln Val Thr Leu Ser
            565
```

(2) INFORMATION FOR SEQ ID NO: 3:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION:1..1653

(xi) SEQUENCE DESCRIPTION: SEQ ID NO: 3:

```
ATG GGT ACT ATA ATT CAA TTT CTG GTG GTC TCC TGT CTA TTG GCA GGA     48
Met Gly Thr Ile Ile Gln Phe Leu Val Val Ser Cys Leu Leu Ala Gly
            570                 575                 580

GCA GGC AGC CCT GAT CCA GCA GCC CTC ATG CAA ATC GGT GTC ATT CCA     96
Ala Gly Ser Pro Asp Pro Ala Ala Leu Met Gln Ile Gly Val Ile Pro
            585                 590                 595

ACA AAT GTC CGG CAA CTT ATG TAT TAT ACT GAG GCC TCA TCA GCA TTC    144
Thr Asn Val Arg Gln Leu Met Tyr Tyr Thr Glu Ala Ser Ser Ala Phe
            600                 605                 610

ATT GTT GTG AAG TTA ATG CCT ACA ATT GAC TCG CCG ATT AGT GGA TGT    192
Ile Val Val Lys Leu Met Pro Thr Ile Asp Ser Pro Ile Ser Gly Cys
        615                 620                 625

AAT ATA ACA TCA ATT TCA AGC TAT AAT GCA ACA CTG ACA AAA CTC CTA    240
Asn Ile Thr Ser Ile Ser Ser Tyr Asn Ala Thr Leu Thr Lys Leu Leu
630                 635                 640                 645

CAG CCG ATC GGT GAG AAT TTG GAA ACG ATT AGG AAC CAG TTG ATT CCA    288
Gln Pro Ile Gly Glu Asn Leu Glu Thr Ile Arg Asn Gln Leu Ile Pro
            650                 655                 660

ACT CGG AGG AGA CGC CGG TTT GCA GGG GTG GTG ATT GGA TTA GCT GCA    336
Thr Arg Arg Arg Arg Phe Ala Gly Val Val Ile Gly Leu Ala Ala
            665                 670                 675

TTA GGA GTA GCT ACT GCC GCA CAG GTC ACT GCC GCA GTA GCA CTA GTA    384
Leu Gly Val Ala Thr Ala Ala Gln Val Thr Ala Ala Val Ala Leu Val
            680                 685                 690

AAG GCA AAT AAA AAT GCT GCG GCT ATA CTC AAT CTC AAA AAT GCA ATC    432
Lys Ala Asn Lys Asn Ala Ala Ala Ile Leu Asn Leu Lys Asn Ala Ile
        695                 700                 705

CAA AAA ACA AAT ACA GCA GTT GCA GAT GTG GTC CAG GCC ACA CAA TCA    480
Gln Lys Thr Asn Thr Ala Val Ala Asp Val Val Gln Ala Thr Gln Ser
710                 715                 720                 725

CTA GGA ACG GCA GTT CAA GCA GTT CAA GAT CAC ATA AAC AGT GTG GTA    528
Leu Gly Thr Ala Val Gln Ala Val Gln Asp His Ile Asn Ser Val Val
            730                 735                 740

AGT CCA GCA ATT ACA GCA GCC AAT TGT AAG GCC CAA GAT GCT ATC ATT    576
Ser Pro Ala Ile Thr Ala Ala Asn Cys Lys Ala Gln Asp Ala Ile Ile
            745                 750                 755

GGC TCA ATC CTC AAT CTC TAT TTG ACC GAG TTG ACA ACT ATC TTC CAC    624
Gly Ser Ile Leu Asn Leu Tyr Leu Thr Glu Leu Thr Thr Ile Phe His
            760                 765                 770

AAT CAA ATT ACA AAC CCT GCA TTG AGT CCT ATT ACA ATT CAA GCT TTA    672
```

|   |   |   |   |   |   |   |   |   |   |   |   |   |
|---|---|---|---|---|---|---|---|---|---|---|---|---|
| Asn | Gln | Ile | Thr | Asn | Pro | Ala | Leu | Ser | Pro | Ile | Thr | Ile | Gln | Ala | Leu |
|   | 775 |   |   |   | 780 |   |   |   |   | 785 |   |   |

```
AGG ATC CTA CTG GGG AGT ACC TTG CCG ACT GTG GTC GAA AAA TCT TTC      720
Arg Ile Leu Leu Gly Ser Thr Leu Pro Thr Val Val Glu Lys Ser Phe
790             795                 800                 805

AAT ACC CAG ATA AGT GCA GCT GAG CTT CTC TCA TCA GGG TTA TTG ACA      768
Asn Thr Gln Ile Ser Ala Ala Glu Leu Leu Ser Ser Gly Leu Leu Thr
                810                 815                 820

GGC CAG ATT GTG GGA TTA GAT TTG ACC TAT ATG CAG ATG GTC ATA AAA      816
Gly Gln Ile Val Gly Leu Asp Leu Thr Tyr Met Gln Met Val Ile Lys
            825                 830                 835

ATT GAG CTG CCA ACT TTA ACT GTA CAA CCT GCA ACC CAG ATC ATA GAT      864
Ile Glu Leu Pro Thr Leu Thr Val Gln Pro Ala Thr Gln Ile Ile Asp
        840                 845                 850

CTG GCC ACC ATT TCT GCA TTC ATT AAC AAT CAA GAA GTC ATG GCC CAA      912
Leu Ala Thr Ile Ser Ala Phe Ile Asn Asn Gln Glu Val Met Ala Gln
    855                 860                 865

TTA CCA ACA CGT GTT ATG GTG ACT GGC AGC TTG ATC CAA GCC TAT CCC      960
Leu Pro Thr Arg Val Met Val Thr Gly Ser Leu Ile Gln Ala Tyr Pro
870                 875                 880                 885

GCA TCG CAA TGC ACT ATT ACA CCC AAC ACT GTG TAC TGT AGG TAT AAT     1008
Ala Ser Gln Cys Thr Ile Thr Pro Asn Thr Val Tyr Cys Arg Tyr Asn
                890                 895                 900

GAT GCC CAA GTA CTC TCA GAT GAT ACG ATG GCT TGC CTC CAA GGT AAC     1056
Asp Ala Gln Val Leu Ser Asp Asp Thr Met Ala Cys Leu Gln Gly Asn
            905                 910                 915

TTG ACA AGA TGC ACC TTC TCT CCG GTG GTT GGG AGC TTT CTC ACT CGA     1104
Leu Thr Arg Cys Thr Phe Ser Pro Val Val Gly Ser Phe Leu Thr Arg
        920                 925                 930

TTC ATG CTG TTC GAT GGA ATA GTT TAT GCA AAT TGC AGG TCG ATG TTA     1152
Phe Met Leu Phe Asp Gly Ile Val Tyr Ala Asn Cys Arg Ser Met Leu
    935                 940                 945

TGC AAG TGC ATG CAG CCT GCT GCT GTG ATC CTA CAG CCG AGT TCA TCC     1200
Cys Lys Cys Met Gln Pro Ala Ala Val Ile Leu Gln Pro Ser Ser Ser
950                 955                 960                 965

CCT GTA ACT GTC ATT GAC ATG TAC AAA TGT GTG AGT CTG CAG CTT GAC     1248
Pro Val Thr Val Ile Asp Met Tyr Lys Cys Val Ser Leu Gln Leu Asp
                970                 975                 980

AAT CTC AGA TTC ACC ATC ACT CAA TTG GCC AAT GTA ACC TAC AAT AGC     1296
Asn Leu Arg Phe Thr Ile Thr Gln Leu Ala Asn Val Thr Tyr Asn Ser
            985                 990                 995

ACC ATC AAG CTT GAA ACA TCC CAG ATC TTG CCT ATT GAT CCG TTG GAT     1344
Thr Ile Lys Leu Glu Thr Ser Gln Ile Leu Pro Ile Asp Pro Leu Asp
        1000                1005                1010

ATA TCC CAG AAT CTA GCT GCG GTG AAT AAG AGT CTA AGT GAT GCA CTA     1392
Ile Ser Gln Asn Leu Ala Ala Val Asn Lys Ser Leu Ser Asp Ala Leu
    1015                1020                1025

CAA CAC TTA GCA CAA AGT GAC ACA TAC CTT TCT GCA ATC ACA TCA GCT     1440
Gln His Leu Ala Gln Ser Asp Thr Tyr Leu Ser Ala Ile Thr Ser Ala
1030                1035                1040                1045

ACG ACT ACA AGT GTA TTA TCC ATA ATG GCA ATC TGT CTT GGA TCG TTA     1488
Thr Thr Thr Ser Val Leu Ser Ile Met Ala Ile Cys Leu Gly Ser Leu
                1050                1055                1060

GGT TTA ATA TTA ATA ATC TTG CTC AGT GTA GTT GTG TGG AAG TTA TTG     1536
Gly Leu Ile Leu Ile Ile Leu Leu Ser Val Val Val Trp Lys Leu Leu
            1065                1070                1075

ACC ATT GTC ACT GCT AAT CGA AAT AGA ATG GAG AAT TTT GTT TAT CAT     1584
Thr Ile Val Thr Ala Asn Arg Asn Arg Met Glu Asn Phe Val Tyr His
        1080                1085                1090

AAT TCA GCA TTC CAC CAC TCA CGA TCT GAT CTC AGT GAG AAA AAT CAA     1632
```

```
Asn Ser Ala Phe His His Ser Arg Ser Asp Leu Ser Glu Lys Asn Gln
    1095                1100                1105

CCT GCA ACT CTT GGA ACA AGA TAA                                              1656
Pro Ala Thr Leu Gly Thr Arg
1110            1115
```

(2) INFORMATION FOR SEQ ID NO: 4:

(i) SEQUENCE CHARACTERISTICS:
        (A) LENGTH: 551 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Gly Thr Ile Ile Gln Phe Leu Val Val Ser Cys Leu Leu Ala Gly
 1               5                  10                  15

Ala Gly Ser Pro Asp Pro Ala Ala Leu Met Gln Ile Gly Val Ile Pro
            20                  25                  30

Thr Asn Val Arg Gln Leu Met Tyr Tyr Thr Glu Ala Ser Ser Ala Phe
        35                  40                  45

Ile Val Val Lys Leu Met Pro Thr Ile Asp Ser Pro Ile Ser Gly Cys
    50                  55                  60

Asn Ile Thr Ser Ile Ser Ser Tyr Asn Ala Thr Leu Thr Lys Leu Leu
65                  70                  75                  80

Gln Pro Ile Gly Glu Asn Leu Glu Thr Ile Arg Asn Gln Leu Ile Pro
                85                  90                  95

Thr Arg Arg Arg Arg Arg Phe Ala Gly Val Val Ile Gly Leu Ala Ala
            100                 105                 110

Leu Gly Val Ala Thr Ala Ala Gln Val Thr Ala Ala Val Ala Leu Val
        115                 120                 125

Lys Ala Asn Lys Asn Ala Ala Ala Ile Leu Asn Leu Lys Asn Ala Ile
    130                 135                 140

Gln Lys Thr Asn Thr Ala Val Ala Asp Val Val Gln Ala Thr Gln Ser
145                 150                 155                 160

Leu Gly Thr Ala Val Gln Ala Val Gln Asp His Ile Asn Ser Val Val
                165                 170                 175

Ser Pro Ala Ile Thr Ala Ala Asn Cys Lys Ala Gln Asp Ala Ile Ile
            180                 185                 190

Gly Ser Ile Leu Asn Leu Tyr Leu Thr Glu Leu Thr Thr Ile Phe His
        195                 200                 205

Asn Gln Ile Thr Asn Pro Ala Leu Ser Pro Ile Thr Ile Gln Ala Leu
    210                 215                 220

Arg Ile Leu Leu Gly Ser Thr Leu Pro Thr Val Val Glu Lys Ser Phe
225                 230                 235                 240

Asn Thr Gln Ile Ser Ala Ala Glu Leu Leu Ser Ser Gly Leu Leu Thr
                245                 250                 255

Gly Gln Ile Val Gly Leu Asp Leu Thr Tyr Met Gln Met Val Ile Lys
            260                 265                 270

Ile Glu Leu Pro Thr Leu Thr Val Gln Pro Ala Thr Gln Ile Ile Asp
        275                 280                 285

Leu Ala Thr Ile Ser Ala Phe Ile Asn Asn Gln Glu Val Met Ala Gln
    290                 295                 300

Leu Pro Thr Arg Val Met Val Thr Gly Ser Leu Ile Gln Ala Tyr Pro
305                 310                 315                 320

Ala Ser Gln Cys Thr Ile Thr Pro Asn Thr Val Tyr Cys Arg Tyr Asn
```

```
                    325                 330                 335
Asp Ala Gln Val Leu Ser Asp Thr Met Ala Cys Leu Gln Gly Asn
            340                 345                 350

Leu Thr Arg Cys Thr Phe Ser Pro Val Val Gly Ser Phe Leu Thr Arg
            355                 360                 365

Phe Met Leu Phe Asp Gly Ile Val Tyr Ala Asn Cys Arg Ser Met Leu
        370                 375                 380

Cys Lys Cys Met Gln Pro Ala Ala Val Ile Leu Gln Pro Ser Ser Ser
385                 390                 395                 400

Pro Val Thr Val Ile Asp Met Tyr Lys Cys Val Ser Leu Gln Leu Asp
                405                 410                 415

Asn Leu Arg Phe Thr Ile Thr Gln Leu Ala Asn Val Thr Tyr Asn Ser
            420                 425                 430

Thr Ile Lys Leu Glu Thr Ser Gln Ile Leu Pro Ile Asp Pro Leu Asp
            435                 440                 445

Ile Ser Gln Asn Leu Ala Ala Val Asn Lys Ser Leu Ser Asp Ala Leu
    450                 455                 460

Gln His Leu Ala Gln Ser Asp Thr Tyr Leu Ser Ala Ile Thr Ser Ala
465                 470                 475                 480

Thr Thr Thr Ser Val Leu Ser Ile Met Ala Ile Cys Leu Gly Ser Leu
            485                 490                 495

Gly Leu Ile Leu Ile Ile Leu Leu Ser Val Val Val Trp Lys Leu Leu
            500                 505                 510

Thr Ile Val Thr Ala Asn Arg Asn Arg Met Glu Asn Phe Val Tyr His
            515                 520                 525

Asn Ser Ala Phe His His Ser Arg Ser Asp Leu Ser Glu Lys Asn Gln
        530                 535                 540

Pro Ala Thr Leu Gly Thr Arg
545                 550
```